(12) United States Patent
Kondo

(10) Patent No.: US 10,538,742 B2
(45) Date of Patent: Jan. 21, 2020

(54) METHODS AND MEANS RELATED TO CANCER STEM CELLS

(75) Inventor: Toru Kondo, Cambridge (GB)

(73) Assignee: Cambridge Enterprise Limited, Cambridgeshire (GB)

( * ) Notice: Subject to any disclaimer, the term of this patent is extended or adjusted under 35 U.S.C. 154(b) by 673 days.

(21) Appl. No.: 11/667,819

(22) PCT Filed: Nov. 12, 2005

(86) PCT No.: PCT/IB2005/003386
§ 371 (c)(1),
(2), (4) Date: Sep. 28, 2007

(87) PCT Pub. No.: WO2006/051405
PCT Pub. Date: May 18, 2006

(65) Prior Publication Data
US 2008/0132423 A1   Jun. 5, 2008

Related U.S. Application Data

(60) Provisional application No. 60/627,639, filed on Nov. 12, 2004.

(51) Int. Cl.
*C12N 5/095*   (2010.01)

(52) U.S. Cl.
CPC .................................. *C12N 5/0695* (2013.01)

(58) Field of Classification Search
None
See application file for complete search history.

(56) References Cited

U.S. PATENT DOCUMENTS

| 6,984,522 B2 * | 1/2006 | Clarke ................. | C12N 5/0695 424/93.1 |
| 7,361,336 B1 * | 4/2008 | Bergstein ............... | C07K 16/30 424/1.49 |
| 7,608,259 B2 * | 10/2009 | Bergstein ............... | C07K 16/30 424/130.1 |
| 8,038,998 B2 * | 10/2011 | Bergstein ............... | C07K 16/30 424/152.1 |
| 2002/0119565 A1 * | 8/2002 | Clarke et al. ................. | 435/366 |
| 2005/0125849 A1 * | 6/2005 | Shmelkov et al. ............. | 800/14 |
| 2005/0232927 A1 * | 10/2005 | Clarke et al. .............. | 424/155.1 |

FOREIGN PATENT DOCUMENTS

| CA | 2447400 A1 | 3/2005 |
| WO | WO 2002/012447 A | 2/2002 |
| WO | WO 2003/102215 A | 12/2003 |
| WO | WO 2004/073630 A | 9/2004 |
| WO | WO 2005/005601 A | 1/2005 |
| WO | WO 2005/089043 A | 9/2005 |
| WO | WO 2006/030473 A | 3/2006 |

OTHER PUBLICATIONS

Kondo et al. Persistence of a small subpopulation of cancer stem-like cells in the C6 glioma cell line, 2003, Proceedings of the National Academy of Sciences, vol. 101, pp. 781-786.*
Kondo et al. Persistence of a small subpopulation of cancer stem-like cells in the C6 glioma cell line, 2003, Proceedings of the National Academy of Sciences, vol. 101, pp. 781-786, provided in the previous action.*
Kondo et al. (Persistence of a small subpopulation of cancer stem-like cells in the C6 glioma cell line, 2004, Proceedings of the National Academy of Sciences, vol. 101, pp. 781-786, previously provided).*
Keiser et al. (Preimplantation Screening for Transgenesis Using an Embryonic Specific Promoter and Green Fluorescent Protein, 2001, Cloning, vol. 3, pp. 23-30).*
Hirschmann-Jax et al (PNAS, 2004, 101:14228-14233, published online Sep. 20, 2004).*
Boulaiz et al (British Journal of Cancer, 2003, 89:192-198).*
Al-Hajj et al., 2003, "Prospective identification of tumorigenic breast cancer cells", Proc Natl Acad Sci USA, 100(7):3983-3988.
Database Accession No. NLM16363650, Setoguchi et al., 2005, "Cancer stem cell in cancer cell lines", Tanpakushitsu Kakusan Koso, 50(15):1995-2000.
Fargeas et al., 2003, "AC133 antigen, CD133, prominin-1, prominin-2, etc.: prominin family gene products in need of a rational nomenclature", Stem Cells, 21(4):506-508.
Hirschmann-Jax et al., 2004, "A distinct "side population" of cells with high drug efflux capacity in human tumor cells", Proc Natl Acad Sci USA, 101(39):14228-14233.
Ignatova et al., 2002, "Human cortical glial tumors contain neural stem-like cells expressing astroglial and neuronal markers in vitro", Glia, 39(3):193-206.
Jamieson et al., 2004, "Granulocyte-macrophage progenitors as candidate leukemic stem cells in blast-crisis CML", The New England Journal of Medicine, 351(7):657-667.
Jordan et al., 2000, "The interleukin-3 receptor alpha chain is a unique marker for human acute myelogenous leukemia stem cells", Leukemia, 14(10):1777-1784.
Kondo et al., 2004, "Persistence of a small subpopulation of cancer stem-like cells in the C6 glioma cell line", Proc Natl Acad Sci USA, 101(3):781-786.
Matsui et al., 2004, "Characterization of clonogenic multiple myeloma cells", Blood, 103(6):2332-2336.
Patrawala et al., 2005, "Side population is enriched in tumorigenic, stem-like cancer cells, whereas ABCG2+ and ABCG2- cancer cells are similarly tumorigenic", Cancer Research, 65(14):6207-6219.

(Continued)

*Primary Examiner* — Laura B Goddard
(74) *Attorney, Agent, or Firm* — McNeill Baur PLLC

(57) ABSTRACT

This invention relates to the methods for the identification and isolation of cancer stem cells from cultured cancer cell lines. Cell line-derived cancer stem cells isolated using the present methods may be useful, for example, in assays to screen compounds for anti-cancer stem cell activity and in target discovery methods for identifying novel expressed genes and druggable targets. The invention also relates to the screening of compounds for activity against cell line-derived cancer stem cells.

16 Claims, 10 Drawing Sheets
Specification includes a Sequence Listing.

(56) References Cited

OTHER PUBLICATIONS

Radtke and Ray, 2003, "The role of Notch in tumorigenesis: oncogene or tumour suppressor?", Nature Reviews Cancer, 3(10):756-767.
Reya et al., 2001, "Stem cells, cancer, and cancer stem cells", Nature, 414(6859):105-111.
Setoguchi et al., 2004, "Cancer stem cells persist in many cancer cell lines", Cell Cycle, 3(4):414-415.
Singh et al., 2003, "Identification of a cancer stem cell in human brain tumors", Cancer Research, 63(18):5821-5828.
Wulf et al., 2001, "A leukemic stem cell with intrinsic drug efflux capacity in acute myeloid leukemia", Blood, 98(4):1166-1173.

* cited by examiner

METHODS AND MEANS RELATED TO CANCER STEM CELLS

This application is a National Stage Application of International Application No. PCT/IB2005/003386, filed Nov. 12, 2005, which is entitled to and claims priority benefit to U.S. provisional application Ser. No. 60/627,639, filed Nov. 12, 2004, each of which is incorporated by reference in its entirety.

FIELD OF THE INVENTION

This invention relates to the identification and isolation of cancer stem cells and the use of the isolated cancer stem cells in assays to screen compounds for anti-cancer stem cell activity and in target discovery methods for identifying novel expressed genes and druggable targets

BACKGROUND OF THE INVENTION

U.S. Pat. No. 6,004,528, incorporated herein by reference, discloses that cancer lesions contain a small but highly virulent sub-population of abnormal stem cells and that these "cancer stem cells" play a significant role in the malignancy of the cancer and in the resistance of the cancer to many standard therapies. Cancer stem cells have been identified, for example, in acute myeloid leukemia (Jordan, C. T., et al (2000) Leukemia 14, 1777-1784), chronic myeloid leukemia (Jamieson, C. H. M., et al (2004) N Engl J Med 351, 657-667), breast cancer (Al-Hajj, M. et al (2003) Proc. Natl. Acad. Sci. USA 100, 3983-3988), brain cancer (Singh, S. K. et al (2003) Cancer Res 63, 5821-5828), multiple myeloma (Matsui, W., et al (2004) Blood 103, 2332-2336), and other cancer types.

The presence of cancer stem cells may lead to recurrences of cancer after treatment. To prevent recurrences, cancer therapies need to eliminate cancer stem cells (Reya T., et al (2001) Nature 414, 105-111).

Stem cells in any tissue, whether normal or malignant, are present in very small numbers and they are difficult to identify and even more difficult to isolate. There is a pressing need for methods to identify and isolate cancer stem cells so that their gene expression profiles, potential drug targets, and properties may be characterized, including their sensitivity to various anti-cancer therapeutic agents and new agents identified through rational drug design or drug screens.

The present invention addresses these and other needs in the art by providing methods for identifying cancer stem cell genes and gene products, i.e., targets, which in turn provide tools for drug discovery, and molecules that identify a cancer cell as a cancer stem cell, e.g., for targeting antibodies. The invention also provides assay systems for discovering or evaluating anti-cancer stem cell-based cancer therapeutics.

SUMMARY OF THE INVENTION

The present inventor has discovered that established cancer cell lines are not homogeneous, even when they have been maintained in culture over extended periods. A sub-population of cells, termed side population (SP), that have stem cell properties can be isolated from established cancer cell lines based on their exclusion of the dye Hoechst 33342. These cell line-derived cancer stem cells act as surrogates for primary tumor-derived cancer stem cells. This finding, i.e. that cancer cell lines harbor cancer stem cell-like SP cells, has subsequently been replicated in the art (Matsui et al (2004) Blood 103: 2332-2336; Hirschman-Jax et al (2004) PNAS USA 101: 14228-14233; Patrawala et al (2005) Cancer Res 65:6207-6219).

Accordingly, the present invention provides methods for identifying and/or obtaining a cell line-derived cancer stem cell comprising providing a population of cancer cells from a cultured cancer cell line, e.g., a human cancer cell line, and determining the presence of a stem cell marker in one or more cells in the population, the presence and/or expression level and/or amount of the marker being indicative that the one or more cells are cell line-derived cancer stem cells. In one example, the cell line-derived cancer stem cell is present in a breast cancer cell line, e.g., MCF-7 or an adenocarcinoma cell line.

Cancer stem cell markers include a verapamil or reserpine sensitive ATP binding cassette (ABC) transporter, e.g., BCRP, or a molecule involved in the Notch, Wnt, or Hedgehog pathway, e.g., Wnt10, Wnt11, Notch 1, Notch 2, or Notch 3. In specific embodiments, the cancer stem cell marker is selected from the group consisting of prominin-1, BCRP, and CD133.

The cell line-derived cancer stem cells identified as described herein may be isolated and/or purified, e.g., by flow cytometry.

Another aspect of the invention provides methods for maintaining and/or culturing one or more cell line-derived cancer stem cells in a serum free medium comprising PDGF and bFGF.

Still another aspect of the invention provides methods of identifying a cancer stem cell marker comprising comparing the expression of one or more nucleic acid molecules in a cell line-derived cancer stem cell with the expression of the one or more nucleic acids in a non-stem cell or normal stem cell or cancer cell that is not a cancer stem cell (a.k.a. tumor bulk), and identifying a nucleic acid molecule whose expression is modulated, e.g., increased in the cell line-derived cancer stem cell relative to the non-stem cell or normal stem cell or tumor bulk as a cancer stem cell marker. In one embodiment, the cancer stem cell is contacted with a test compound and the level and/or expression of the cancer stem cell marker nucleic acid molecule is determined.

The invention also provides methods of identifying a cancer stem cell marker comprising comparing the level or amount of one or more polypeptides in a cell line-derived cancer stem cell with the level or amount of one or more polypeptides in a non-stem cell or normal stem cell or tumor bulk, and identifying a polypeptide from the one or more polypeptides whose level or amount is modulated, e.g., increased in the cancer stem cell relative to the non-stem cell or normal stem cell or tumor bulk as a cancer stem cell marker polypeptide. In one embodiment, the invention provides methods for producing an antibody that binds to the identified cancer stem cell marker polypeptide.

Drug screens typically employ cancer cell lines, or some derivative thereof, and this process selects for compounds which target the bulk of the cell line, not the cell line-derived cancer stem cell sub-population. Cell line-derived cancer stem cells identified and purified as described herein are therefore useful in the development of more effective cancer therapies.

In a further aspect, the invention provides methods of identifying and/or obtaining a compound having anti-cancer stem cell activity for use in the treatment of a cancer condition comprising contacting a cell line-derived cancer stem cell isolated by a method described herein with a test compound, and determining preferential binding of the test compound to the cell line-derived cancer stem, cell. In one embodiment, an increase in binding to the cell line-derived cancer stem cell relative to a non-stem cell or normal cell is indicative that the compound is useful in the treatment of a cancer condition.

In another aspect, the invention provides methods of identifying and/or obtaining a compound for use in the treatment of a cancer condition comprising contacting a cell line-derived cancer stem cell with a test compound, and determining modulation of growth, proliferation, viability, and/or differentiation status of the cell in the presence of the test compound as compared to the growth, proliferation, viability, and/or differentiation status of a cell line-derived cancer stem cell in the absence of the compound. In one embodiment, a decrease in growth, viability, and/or proliferation of the cell line-derived cancer stem cell is indicative that the compound is useful in the treatment of a cancer condition. In another embodiment, the test compound is an antibody or a small molecule. In yet another embodiment, the method is a high throughput screening method.

Other features and advantages of the instant invention will be apparent from the following detailed description and examples which should not be construed as limiting. The contents of all references, Accession numbers, Genbank entries, patents and published patent applications cited throughout this application are expressly incorporated herein by reference.

DETAILED DESCRIPTION

Figure 1:
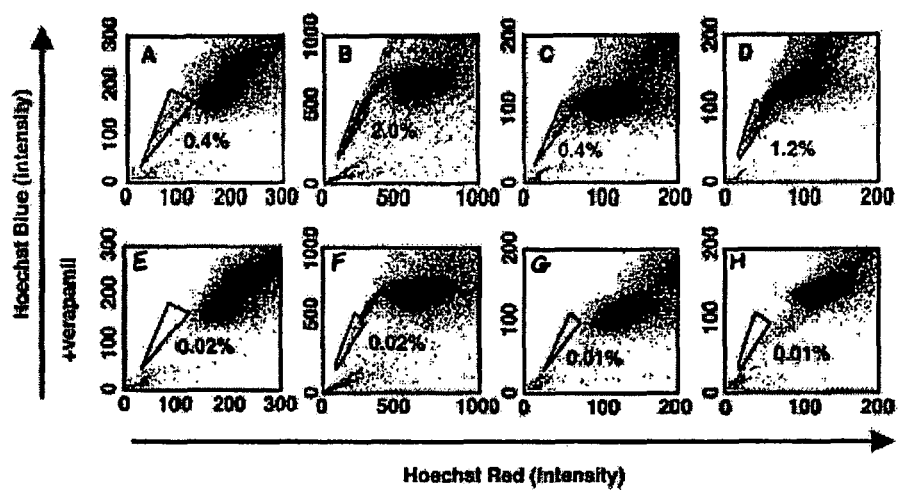
FIG. 1A-1H shows the existence of SP cells in established cancer cell lines. Cells of the rat C6 glioma (A, E), human MCF7 breast carcinoma (B, F), rat B104 neuroblastoma (C, G), and human HeLa carcinoma (D, H) cell lines were labeled with Hoechst 33342 and then analyzed by flow cytometry. (E H) Results when the cells were treated with 50-μM verapamil during the labeling procedure are also shown. The SP, which disappears in the presence of verapamil, is outlined and shown as a percentage of the total cell population. These experiments were repeated at least three times with similar results.

The present invention is directed, at least in part, to the use of cancer cell lines, commercially available or otherwise, for the identification and isolation of SP cells containing cancer stem cells. As used herein, the term "side population" or "SP" refers to a subset of cells isolated from or identified within a larger cell population, e.g., a cancer cell line, which contains cancer stem cells. Accordingly, cancer stem cells obtained from a cancer cell line are termed "cell line-derived cancer stem cells."

In another aspect, the invention provides methods for identifying cancer stem cell markers. In still another aspect, the present invention includes screening methods, including high throughput screening methods, utilizing cell line-derived cancer stem cells, to identify anti-cancer compounds as well as subsequent testing of such identified candidate compounds for anti-cancer activity. In yet another aspect, the invention provides methods for the treatment of cancer in a subject comprising administering an anti-cancer compound identified by the methods described herein. Furthermore, the invention provides methods for culturing cancer stem cells.

In the methods of the invention, there is often a comparison of a cell line-derived cancer stem cell with a non-cancer stem cell. Non-cancer stem cells include the cancer cell line from which the cell line-derived cancer stem cell was obtained and primary bulk tumor cells (cancer cells) of the same type of cancer as the cancer cell line. For example, and not by way of limitation, in the case of cell line-derived cancer stem cells from the MCF-7 human breast cancer cell line, the non-cancer stem cell can either be bulk MCF-7 cells or primary breast cancer cells. Similarly, in the case of a cell line-derived cancer stem cell from the U-20S or SaOS-2 cancer cell line, bulk tumor cells from that line or from a primary osteosarcoma would be non-cancer stem cells.

One aspect of the invention provides a method of identifying and/or obtaining a cell line-derived cancer stem cell comprising;

providing a population of cancer cells from a cultured cancer cell line, and;

determining the presence of a stem cell marker in one or more cells in the population, the presence of the marker being indicative that the one or more cells are cell line-derived cancer stem cells.

In one embodiment, cultured cancer cells are cells from established cancer cell lines that have undergone numerous passages in vitro.

Cancer cell lines are initially derived from cancerous tissue, for example primary or metastatic tumours, but have been maintained in a culture for an extended period. Such cells can be reproduced indefinitely in vitro (i.e., they are continuous cell lines) and have a potentially unlimited lifespan in culture.

Cultured cancer cell lines generally consist of a single cell type and are distinct from primary cell cultures, which generally consist of a mixed population of cell types, many of which will only survive for one or a few passages before dying.

Many cancer cell lines suitable for use in the present methods are known, including adenocarcinoma cell lines such as HeLa, prostate cancer cell lines, lung cancer cell lines, gastrointestinal cancer cell lines, bowel cancer cell lines, colon cancer cell lines, breast carcinoma cell lines such as MCF7, ovarian carcinoma cell lines, testicular cancer cell lines, glioma cell lines such as C6, liver cancer cell lines, kidney cancer cell lines, bladder cancer cell lines, pancreatic cancer cell lines, brain cancer cell lines, neuroblastoma cell lines such as B104, sarcoma cell lines, osteosarcoma cell lines, melanoma cell lines, lymphoma cell lines, retinoblastoma cell lines, skin cancer cell lines, leukemia cell lines, and lymphoma cell lines.

A wide range of suitable cancer cell lines are available from commercial sources, including European Collection of Cell Cultures (ECCC; Salisbury, UK), American Type Culture Collection (ATCC; Manassas, USA), Coriell Institute for Medical Research (USA), Riken Bioresource Center (Japan), and Japanese Collection of Research Bioresources (Japan).

In one embodiment, the cultured cancer cells are human cancer cells.

In some embodiments, cultured cancer cells exclude osteosarcoma cells.

A cell line-derived cancer stem cell is a member of a sub-population of cells within the population of cultured cancer cells that possesses one or more stem cell properties, e.g., the expression of a stem cell marker.

A cancer stem cell is able to generate both cancer stem cells and non-stem cells in culture (unlike other cells in the population) and can also generate cells of different lineages both in vitro and in vivo. Furthermore, cancer stem cells are shown herein to be largely responsible for in vivo malignancy. A cell line-derived cancer stem cell is similarly able to generate both cancer stem cells and non-stem cells in culture. As exemplified herein, a cell line-derived cancer stem cell can also establish a tumor in vivo.

Cancer stem cell markers suitable for use in the present methods include any marker whose expression is increased or decreased in a cancer stem cell relative to a non-cancer stem cell. Cancer stem cell markers suitable for use in the present methods also include any marker whose expression is increased or decreased in a cancer stem cell relative to vital normal (non-neoplastic) stem cells and/or tissues.

Many stem cell markers are known in the art, including, for example stem cell factor, (SCF or c-Kit ligand), telomerase, TRA-1-60, TRA-1-81, vimentin, genesis, germ cell nuclear factor, hepatocyte nuclear factor-HNF-4, nestin, breast cancer resistance protein (BCRP), NG2, A2B5, polysialylated form of neuronal cell-adhesion molecule (PSA-NCAM), nucleostemin, sox-2, musashi-1 and -2, hairy and enhancer-of-splits (Hes-1, -3, -5), melk, PSP, Inhibitor of differentiation (Id-1, -2, -3, -4), Bmi-1, brca-1, Oct-4, Nanog, FGF-4, Pax6, Stage-specific embryonic antigens (SSEA-1, -3, -4), Cluster designation 30 (CD30), CD34, CD44, Notch, CD123, CD133, CD24, Cripto (TDGF-1) ATA-4 gene, GCTM-2, Alkaline phosphatase, Alpha-fetoprotein (AFP), Bone morphogenetic protein-4, mdr-1, hiwi, prominin-1 and Brachyury. Also, certain signaling pathways and the proteins that make up these signaling pathways have been associated with stem cell biology and renewal of stem cells. These include the Wnt, Notch, and Hedgehog pathways. Molecules involved in these pathways, including, but not limited to Wnt1, Wnt10, Wnt11, Notch 1, Notch 2, Notch 3, and Notch 4, are also included as stem cell markers as defined herein.

The Notch family of receptors has been implicated in stem cell development and differentiation (see, Morrison et al., Cell 101(5): 499-510 (2000); Artavanis-Tsakonas et al., Science 284: 770 (1999); and Artavanis-Tsakonas et al., Science 268: 225-232 (1995); U.S. Pat. No. 6,090,922, incorporated by reference). There are four known mammalian Notch family members. Notch 4 is the human ortholog of the mouse int-3 oncogene that plays a role in breast cancer in mice. Gallahan et al., Cancer Res. 56(8): 1775-85 (1996); Uyttendaele et al., Development 2122: 251 (1996); Imatani & Callahan, Oncogene 19(2): 223-31 (2000), incorporated herein by reference). Molecules involved in the Wnt pathway are described in U.S. Pat. No. 6,159,462, the contents of which are incorporated herein by reference. Hedgehog pathway-related molecules are described in U.S. Pat. No. 6,291,516, the contents of which are incorporated by reference.

Certain differentiation markers have also been associated with stem cells as well, including integrin alpha-6, mucin-1 (EMA), estrogen receptor-alpha, estrogen receptor-beta, cytokeratin-14, cytokeratin-18, and cytokeratin 19, and are also included as stem cell markers.

For example, CD34 has been used to isolate leukaemic stem cells ((Wulf, G. G. et al. (2001) supra)) and both CD24 and CD44 have been used to isolate breast cancer stem cells (Al-Hajj, M. et al (2003) supra).

In some embodiments, the marker may be a verapamil or reserpine sensitive ATP-binding cassette (ABC) transporter. The ABC transporter BCRP (Gottesman et al (2002) *Nat. Rev. Cancer* 2, 48-58; Zhou, S. et al. (2001) *Nat. Med.* 7, 1028-1034; Zhou, S. et al (2002) *Proc. Natl. Acad. Sci. USA* 99, 12339-12344; Bunting, K. D. (2002) Stem Cells (Dayton) 20, 11-20) is shown herein to be a useful stem cell marker. The sequence of mouse bcrp has the Genbank accession numbers BC053730 and AF140218, the sequence of human bcrp has the Genbank accession numbers AB056867, AY017168, and BC021281, and the sequence of RAT bcrp has the Genbank accession number AB094089.

The presence of a cancer stem cell marker on a cell may be determined by any convenient method.

In some embodiments, the expression of a marker may be determined at the polypeptide level, by determining the presence or level of a stem cell marker polypeptide in or on the surface of the cell. For example, the binding of a cultured cancer cell to an antibody that binds specifically to stem cell marker may be determined. Many techniques and methodologies for determining the binding of antibodies to cell antigens are known in the art. Suitable methodologies include fluorescence activated cell sorting (FACS), immunohistochemical staining, immunocytochemical staining, Western Blotting, immunofluorescence, enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. All of these approaches are well known in the art. For example, in one embodiment of the invention, antibodies specific for BCRP, Notch, or CD133 may be used to specifically identify cell line-derived cancer stem cells in the breast cancer cell line, MCF-7. For example, in one embodiment, these antibodies are incubated with cultures of MCF-7 cells and the cells are separated to identify the cell line-derived cancer stem cell sub-population by flow cytometry.

In some embodiments, the expression of a marker may be determined at the nucleic acid level, by determining the expression of a nucleic acid, for example mRNA, encoding a cancer stem cell marker. Many suitable techniques are available, for example Northern blot, RNAse protection, RT-PCR, real-time PCR, microarrays, and serial analysis of gene transcription (SAGE). For example, in one embodiment of the invention, cell line-derived cancer stem cells are isolated from the human breast cancer cell line, MCF-7, e.g., by flow cytometry using fluorescent Hoechst dye exclusion or fluorescent antibodies to a cancer stem cell marker, e.g., BCRP, Notch, or CD133. Gene expression analysis of certain candidate genes can then be performed by RT-PCR on these isolated cell line-derived cancer stem cells. In this example, the non-cancer stem cell population (whether cell line cells or primary tumor cells from the same type of tumor) may be used as a control. This analysis will elucidate gene products that are differentially expressed in cancer stem cells. The method of gene expression analysis by RT-PCR is widely available to one skilled in the art.

In some embodiments, the presence of a stem cell marker may be determined using a functional assay. The presence of a verapamil or reserpine sensitive ABC marker may be determined, for example, by contacting the cells with a fluorescent dye and determining the expulsion of dye from the cell. In particular, the expulsion of dye in the presence and absence of verapamil or reserpine may be determined. Suitable fluorescent dyes include Hoechst 33342. Other suitable dyes include Rhodamine 123.

Cells that expel fluorescent dye, in particular in the absence relative to the presence of verapamil or reserpine, may be identified as expressing a verapamil or reserpine sensitive ABC marker and may therefore be candidate cancer stem cells.

The expulsion of fluorescent dye by a cell may be determined by any convenient method, including fluorescence activated cell sorting (FACS).

A cultured cell identified as expressing a cancer stem cell marker may be isolated and/or purified from the cultured cell population. Any convenient method may be used. In some embodiments, methods which allow the identification of the marker and the isolation of the expressing cell in a continuous process may be employed. Suitable methods include fluorescence activating cell sorting (FACS).

In other embodiments, cell line-derived cancer stem cells may be isolated and/or purified from the cultured cell population using antibodies which bind specifically to stem cell markers. Suitable markers include CD133, BCRP, Notch 1, Notch 2, and CD34. Suitable methods include conventional affinity column chromatography and/or magnetic bead separation.

In other embodiments, cell line-derived cancer stem cells may be isolated and/or purified from the cultured cell population using negative selection using an antibody which binds to cancerous non-stem cells but does not bind to cancer stem cells. For example, CD138 has been shown to be present on the bulk but not the cancer stem cell population of multiple myeloma (Matsui, W., et al (2004) Blood 103, 2332-2336).

Cell line-derived cancer stem cells isolated and/or purified as described herein may be analysed (e.g., for gene expression) de novo or may be maintained and/or cultured in vitro. Suitable methods and reagents for maintaining cells in culture are well known in the art. For example, a standard medium, such as Dulbeccos Modified Eagle Medium (DMEM) supplemented with 10% fetal calf serum (FCS), 100 units/ml penicillin G, and 100 µg/ml streptomycin may be used.

In one embodiment, cells may be suspended or immersed in a serum free medium that comprises basic fibroblast growth factor (bFGF) and platelet-derived growth factor (PDGF), for example at 5 to 100 ng/ml, e.g, about 5 ng/ml, 10 ng/ml, 20 ng/ml, 30 ng/ml, 40 ng/ml, 50 ng/ml, 60 ng/ml, 70 ng/ml, 80 ng/ml, 90 ng/ml or 100 ng/ml. Cells may then be cultured using conventional techniques.

Cell line-derived cancer stem cells identified and/or obtained using the present methods are useful for a wide range of applications, for example for the development of cancer therapies. In particular, cells may be useful in the production of antibodies that bind to cell line-derived cancer stem cells and to identify cancer stem cell-associated antigens and markers.

In some embodiments, cancer stem cell-associated antigens and markers may be identified at the nucleic acid level.

For example, in one embodiment, a method of identifying a cancer stem cell-associated nucleic acid molecule comprises;
  comparing the expression of one or more nucleic acid molecules in a cell line-derived cancer stem cell obtained from a population of cultured cancer cells by a method described herein with the expression of the one or more nucleic acid molecules in a non-stem cell, and;
  identifying a nucleic acid molecule whose expression is modulated, e.g., increased or decreased in the cell line-derived cancer stem cell relative to the non-stem cell as a cancer stem cell-associated nucleic acid molecule.

In some embodiments, a method of identifying a cancer stem cell-associated nucleic acid molecule comprises;
  comparing the expression of one or more nucleic acid molecules in a cancer stem cell obtained from a population of cultured cancer cells by a method described herein with the expression of the one or more nucleic acid molecules in a normal (non-neoplastic) stem cell and/or tissue, and;

identifying a nucleic acid molecule whose expression is modulated, e.g., increased or decreased in the cell line-derived cancer stem cell relative to the normal (non-neoplastic) stem cell and/or tissue as a cancer stem cell-associated nucleic acid molecule.

The stem cell-associated nucleic acid molecule may be cloned and expressed to produce a recombinant stem cell-associated polypeptide.

A test compound, for example an inhibitory polynucleotide, including antisense or double-stranded RNA (RNA interference) or an inhibitory molecule such as an aptamer, may be screened for ability to block the cancer stem cell-associated nucleic acid and/or to impair cell line-derived cancer stem cell growth and/or viability.

Methods for the cloning and expression of nucleic acids to produce recombinant polypeptides are well known in the art.

In some embodiments, cancer stem cell-associated antigens and markers may be identified at the polypeptide level.

For example, in one embodiment, a method of identifying a cancer stem cell-associated polypeptide comprises;

comparing the level or amount of one or more polypeptides in a cell line-derived cancer stem cell obtained from a population of cultured cancer cells by a method described herein with the level or amount of the one or more polypeptides in a non-stem cell, and;

identifying a polypeptide from the one or more polypeptides whose level or amount is modulated, e.g., increased or decreased in the cell line-derived cancer stem cell relative to the non-stem cell as a cancer stem cell-associated polypeptide.

In some embodiments, a method of identifying a cancer stem cell-associated polypeptide comprises;

comparing the level or amount of one or more polypeptides in a cell line-derived cancer stem cell obtained from a population of cultured cancer cells by a method described herein with the level or amount of the one or more polypeptides in a normal (non-neoplastic) stem cell and/or tissue, and;

identifying a polypeptide whose expression is modulated, e.g., increased in the cell line-derived cancer stem cell relative to the normal (non-neoplastic) stem cell and/or tissue as a cancer stem cell-associated polypeptide.

The stem cell-associated polypeptide may be isolated and/or purified. An isolated polypeptide may be investigated further. For example, it may be sequenced using methods well-known in the art.

Cancer stem cell-associated polypeptides may be useful for example in the production of cancer stem cell-specific antibodies. These antibodies may be useful in a range of applications, including cancer therapy, and are discussed in more detail below.

The present invention also includes high-throughput methods for identifying cancer stem cell markers. For example, cell line-derived cancer stem cells may be tested for the expression of any of a panel of candidate gene products by, for example, RT-PCR using methods that are widely available to one skilled in the art. Non-cancer stem cells, or normal stem cells may be used as control cells.

Other aspects of the invention relate to methods of expanding a sub-population of cancer-stem cells isolated from a cancer cell line.

In one embodiment, a method of culturing a cancer stem cell, particularly a cell line-derived cancer stem cell, comprises;

suspending the cell in a serum-free medium comprising PDGF and bFGF, and;

causing or allowing the cell to proliferate in the medium.

Suitable serum free media are well-known in the art. For example, Dulbeccos Modified Eagle Medium supplemented with 10 µg/ml bovine insulin, 100 µg/ml human transferrin, 100 µg/ml BSA, 60 ng/ml progesterone, 16 putrescine, 40 ng/ml sodium selenite, 63 µg/ml, N-acetylcysteine, 5 µM forskolin, 50 units/ml penicillin, and 50 µg/ml streptomycin, as well as 10 ng/ml bFGF and 10 ng/ml PDGF may be used.

Cells may, for example, be maintained in a suitable culture vessel at about 37° C. in a humidified 5% $CO_2$/95% air atmosphere.

A medium suitable for the expansion or maintenance of a cancer stem cell, and particularly a cell line-derived cancer stem cell, population may be produced by providing a serum free growth medium, and supplementing the medium with PDGF and bFGF.

PDGF and bFGF cytokines may be mammalian, more preferably human and may be conveniently obtained from commercial suppliers (e.g., PeproTech (Rocky Hill, N.J.)).

Suitable concentrations of PDGF and bFGF in the medium are about 5 to 100 ng/ml, e.g. about 5 ng/ml, 10 ng/ml, 20 ng/ml, 30 ng/ml, 40 ng/ml, 50 ng/ml, 60 ng/ml, 70 ng/ml, 80 ng/ml, 90 ng/ml or 100 ng/ml.

Cancer stem cells are shown herein to be play a significant role in the malignancy of cancer conditions. Therefore, compounds that specifically target these cells may be useful as anti-cancer therapeutics. Accordingly, the present invention also includes the use of cancer stem cell-specific antibodies and cell line-derived cancer stem cells, e.g., cell line-derived cancer stem cells identified from cancer cell lines, as described herein, to screen test compounds to identify candidate compounds having anti-cancer stem cell activity. The screening of test compounds for anti-cancer stem cell activity overcomes many of the limitations associated with classic drug screening, which tests compounds only for activity against the entire cell line (i.e., with no cell line-derived cancer stem cell readout). Also, cell line-derived cancer stem cells identified in cancer cell lines can be used as surrogates for the study of cancer stem cells from primary human tissues. The use of cell lines overcomes many of the limitations associated with testing drugs using primary tissue since primary cancer tissue is of finite supply for a given experiment. Accessing additional primary tissues interrupts the reproducibility of an experiment which is not the case when cell lines are used. In addition, primary tissues, since finite, cannot be immortally transfected with promoter-reporter constructs in the way cell lines can. Also, cancer cell lines provide a virtually unlimited source of cells that behave as cancer stem cells, enabling the screening of large numbers of compounds in a single experiment, and reproducibly so. The ability of cancer cell lines to be scaled-up as needed enables the testing of large compound libraries (high throughput screens).

A "test compound" is a molecule that can be tested for its ability to act as a modulator of the growth, proliferation, viability, and/or differentiation status of a cancer stem cell, its ability to act as a modulator of a gene or gene product expression or activity, or its ability to bind to a cancer stem cell. Test compounds can be selected without limitation from small inorganic and organic molecules (i.e., those molecules of less than about 2 kD, and more preferably less than about 1 kD in molecular weight), polypeptides (including native ligands, antibodies, antibody fragments, and other immunospecific molecules), oligonucleotides and polynucleotide molecules, e.g., antisense and interfering RNA, and derivatives thereof. A compound that modulates the growth, proliferation, viability, and/or differentiation status of a cell line-derived cancer stem cell, binds to a cell line-derived cancer stem cell, or modulates the expression or activity of a nucleic acid or protein expressed by a cell line-derived cancer stem cell is designated herein as a "candidate compound" or "lead compound" suitable for further testing and development.

Suitable test compounds include compounds identified as binding to cell line-derived cancer stem cells using methods described herein. In one embodiment of the invention, a cancer cell line is treated with a gamma secretase inhibitor, and the effect on the cell line-derived cancer stem cell population is then monitored by flow cytometry using Hoechst dye exclusion or using an antibody that specifically binds to cell line-derived cancer stem cells in combination with a marker for apoptosis (e.g., Annexin, or Propidium Iodide).

The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) Anticancer Drug Des. 12:145).

Examples of methods for the synthesis of molecular libraries can be found in the art, for example in: DeWitt et al. (1993) Proc. Natl. Acad. Sci. U.S.A. 90:6909; Erb et al. (1994) Proc. Natl. Acad. Sci. USA 91:11422; Zuckermann et al. (1994). J. Med. Chem. 37:2678; Cho et al. (1993) Science 261:1303; Carrell et al. (1994) Angew. Chem. Int. Ed. Engl. 33:2059; Carell et al. (1994) Angew. Chem. Int. Ed. Engl. 33:2061; and in Gallop et al. (1994) J. Med. Chem. 37:1233.

Libraries of compounds may be presented in solution (e.g., Houghten (1992) Biotechniques 13:412-421), or on beads (Lam (1991) Nature 354:82-84), chips (Fodor (1993) Nature 364:555-556), bacteria (Ladner U.S. Pat. No. 5,223,409), spores (Ladner U.S. Pat. No. '409), plasmids (Cull et al. (1992) Proc. Natl. Acad. Sci. USA 89:1865-1869) or on phage (Scott and Smith (1990) Science 249:386-390); (Devlin (1990) Science 249:404-406); (Cwirla et al. (1990) Proc. Natl. Acad. Sci. 87:6378-6382); (Felici (1991) J. Mol. Biol. 222:301-310); (Ladner supra.).

One embodiment of the present invention includes the use of cancer cell lines as a source of cancer stem cells for use in such screens, including high throughput screens.

The invention also includes the use of cancer stem cell-specific antibodies to monitor the growth, proliferation, and/or viability of the cell line-derived cancer stem cell population of cancer cell lines for use in drug screens and the development of assays for drug screens, including high throughput screens.

Another aspect of the invention provides a method of identifying and/or obtaining an anti-cancer compound comprising:
    contacting a cell isolated by a method described herein with a test compound, and;
    determining binding of the compound to the cell.

Binding may be determined relative to binding to a non-stem cell, for example a cancer cell or a normal non-cancer cell, or a normal stem cell.

An increase in binding to a cell line-derived cancer stem cell relative to a non-stem cell may be indicative that the compound is an anti-cancer compound.

Binding of a compound to a cell may be determined using any one of numerous methodologies known in the art.

Alternatively and/or additionally to detecting or measuring binding, the effect of a test compound on the growth and/or proliferation of a cell line-derived cancer stem cell may be determined.

A method of identifying and/or obtaining an anti-cancer compound comprises
    contacting a cell isolated by a method described herein with a test compound, and;
    determining the growth, proliferation, viability, and/or differentiation status of the cell in the presence of the compound.

The growth, proliferation, viability, and/or differentiation status of the cell may be determined relative to binding to a non-stem cell, for example a cancer cell or a normal non-cancer cell, or a normal stem cell.

A decrease in the growth, proliferation, and/or viability or a change in the differentiation status of the cell in the presence relative to the absence of test compound is indicative that the test compound is a candidate compound for the treatment of a cancer condition.

Growth, proliferation, viability, and/or differentiation status may be determined using any convenient technique.

Another method of identifying and/or obtaining an anti-cancer compound comprises
    contacting a cell isolated by a method described herein with a test compound, and;
    determining the modulation in expression or activity of a cancer stem cell marker in the presence of the compound as compared to the expression or activity of the cancer stem cell marker in the absence of the compound.

Another method of identifying and/or obtaining an anti-cancer compound comprises
    contacting a cell isolated by a method described herein with a test compound, and;
    a change in the morphology of the cell line-derived cancer stem cell in the presence of the test compound.

In another embodiment, the cell line-derived cancer stem cells are monitored in the presence of a test compound, e.g., via fluorescent antibody- or promoter-based reporters, to identify compounds with anti-cancer stem cell activity.

In yet another embodiment of the invention, high throughput screening of test compounds comprises synthesis of large numbers of different test compounds, e.g., a library of test compounds. Several methods of automated assays that have been developed in recent years enable the screening of tens of thousands of compounds in a short period of time (see, e.g., U.S. Pat. Nos. 5,585,277, 5,679,582, and 6,020,141, incorporated herein by reference). In one embodiment, the test compounds may be linked to a solid substrate. In another embodiment, the test compounds are contacted with cell line-derived cancer stem cells, or molecules isolated from such cells. Cell line-derived cancer stem cells that are bound to one or more test compounds are then detected by methods well known in the art. In one embodiment, automated methods may be used to identify compounds that bind to cancer stem cells.

In another embodiment, a high throughput assay of the invention comprises measuring a response of the target cells (cell line-derived cancer stem cells) that provides detectable evidence that the test compound may have anti-cancer stem cell activity. For example, a response includes binding to a test compound, modulation in the growth, proliferation, viability, and/or differentiation status of the cell line-derived cancer stem cell, modulation in expression or activity of a cancer stem cell marker, or changes in morphology of the cell line-derived cancer stem cell. A detectable signal is compared to control cells. Techniques such as differential display, representational difference analysis (RDA), GEM-Gene Expression Microarrays (U.S. Pat. No. 5,545,531), suppressive subtraction hybridization (SSH) and direct sequencing (PCT patent application WO 96/17957) can be used in the high throughput screening methods of the invention. In one embodiment of the invention, cell line-derived cancer stem cells are not isolated from the cell line, but rather are maintained within the cell line and labeled with an antibody or a promoter-reporter, the expression of which is preferentially expressed by the cancer stem cells. In this way, this assay can be used to screen compounds (e.g., in a high throughput screen) for activity against cancer stem cells. One example of this method comprises the use of this assay in combination with markers of cell death, proliferation, or differentiation (e.g. Annexin, propidium iodide, etc) to identify compounds that affect cancer stem cells. In one embodiment, compounds that affect cancer stem cells may be identified using flow cytometry. In another embodiment, compounds that affect cancer stem cells may be identified using methods other than flow cytometry, such as fluorimetry.

Appropriate control experiments may be performed in accordance with appropriate knowledge and practice of the ordinary skilled person.

Antibody molecules are one class of test compounds suitable for screening as anti-cancer agents.

An antibody molecule includes any binding substance having an immunoglobulin-binding domain with the required specificity, including modified and unmodified antibodies, antibody fragments and derivatives.

Exemplary antibody fragments which are capable of binding an antigen or other binding partner are the Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F(ab')2 fragments, a bivalent fragment including two Fab fragments linked by a disulphide bridge at the hinge region. Single chain Fv fragments are also included.

An antibody molecule may be identified and/or obtained which binds specifically to cancer stem cells. In other words, an antibody molecule may bind preferentially to stem cells relative to non-stem cells within a population of cultured cancer cells. In some embodiments, antibody molecules may bind preferentially to cell line-derived cancer stem cells within the population of cultured cancer cells relative to non-cancer cells from the organism from which the cultured cells were derived.

Preferential or specific binding of an antibody molecule is characterised by a binding affinity for a target antigen, such as a cancer stem cell antigen, that is substantially higher than its binding affinity to other antigens, including antigens expressed by cells which are not cancer stem cells. For example, an antibody may bind to the target antigen with at least 5 fold, at least 10 fold, at least 20 fold, or at least 100 fold greater affinity than other non-target antigens.

Preferably, an antibody molecule shows little or no binding to non-cancer cells, in particular little or no binding to non-cancer cells from the organism from which the cultured cells were derived.

The reactivity of an antibody molecule with a target antigen may be determined in methods of the invention by any appropriate means. Suitable protocols are well known in the art (see for example Antibodies: A Laboratory Manual E. Harlow and D. Lane, Cold Spring Harbor Laboratory Press, N Y, 1988). Tagging with individual reporter molecules is one possibility. The reporter molecules may directly or indirectly generate detectable, and preferably measurable, signals. The linkage of reporter molecules may be directly or indirectly, covalently, e.g., via a peptide bond or non-covalently. Linkage via a peptide bond may be as a result of recombinant expression of a gene fusion encoding antibody and reporter molecule. The actual mode of determining the binding of an antibody molecule is not a feature of the invention and those skilled in the art are able to choose a suitable mode according to their preference and general knowledge.

Antibody molecules for use in the present methods may be produced using methods which are standard in the art. Methods of producing antibodies include immunising a mammal (e.g., mouse, rat, rabbit, horse, goat, sheep or monkey) with a cell line-derived cancer stem cell or a cancer stem cell antigen, e.g., identified in a cell line-derived cancer stem cell. Antibodies may be obtained from immunised animals using any of a variety of techniques known in the art, and screened, preferably using binding of antibody to antigen of interest. For instance, Western blotting techniques or immunoprecipitation may be used (Armitage et al., 1992, Nature 357: 80-82). Isolation of antibodies and/or antibody-producing cells from an animal may be accompanied by a step of sacrificing the animal.

A method of producing an antibody molecule which binds to a cancer stem cell comprises;
  introducing a cell line-derived cancer stem cell or a cancer stem cell antigen obtained by a method described above to a test animal;
  removing a sample of serum from the animal and, identifying one or more antibody molecules in the sample which bind to the cell line-derived cancer stem cell or antigen.

In some embodiments, cells may be fixed by 4% paraformaldehyde and then used for immunization in order to generate antibodies specific for cell-surface molecules.

The preferential or specific binding of one or more antibody molecules in the sample to a cell line-derived cancer stem cell relative to other cell types may be determined.

As an alternative or supplement to immunising a mammal with a cell, polypeptide or peptide, an antibody specific for a cell line-derived cancer stem cell or cancer stem cell antigen may be obtained from a recombinantly produced library of expressed immunoglobulin variable domains, e.g., using lambda bacteriophage or filamentous bacteriophage which display functional immunoglobulin binding domains on their surfaces; for instance see WO92/01047. The library may be naive, that is constructed from sequences obtained from an organism which has not been immunised with any of the proteins (or fragments), or may be one constructed using sequences obtained from an organism which has been exposed to the antigen of interest.

A method of producing an antibody molecule which binds to a cancer stem cell comprises;

contacting a population of antibody molecules with a cell line-derived cancer stem cell obtained by a method described herein and;

identifying one or more antibody molecules in the population which bind to the cell line-derived cancer stem cell.

The preferential or specific binding of one or more antibody molecules in the population to a cancer stem cell relative to other cell types may be determined.

A further aspect of the invention provides an antibody molecule produced by a method described herein.

Other test compounds for use in methods of the invention may be natural or synthetic chemical compounds used in drug screening programmes. Extracts of plants which contain several characterised or uncharacterised components may also be used. Combinatorial library technology (Schultz, J S (1996) Biotechnol. Prog. 12:729-743) provides an efficient way of testing a potentially vast number of different substances for ability to modulate the activity of a polypeptide.

The amount of test substance or compound which may be added will normally be determined by trial and error depending upon the type of compound used.

Typically, from about 0.0001 to 10 mM concentrations of putative inhibitor compound may be used, for example from 1 to 100 μM.

A method as described herein may comprise the step of identifying a test compound as a compound having anti-cancer stem cell activity, e.g., a compound which affects the cancer stem cell growth, proliferation, viability, and/or differentiation status, modulates expression or activity of a cancer stem cell marker, which is therefore a candidate anti-cancer compound.

Following identification of a compound having anti-cancer stem cell activity, e.g., a compound which affects cell line-derived cancer stem cell growth, proliferation, viability, and/or differentiation status or modulates expression or activity of a cancer stem cell marker, the compound may be investigated further, in particular for its ability to reduce or inhibit the progression of a cancer condition in an animal or individual.

The test compound may be isolated and/or purified or alternatively it may be synthesised using conventional techniques of recombinant expression or chemical synthesis. Furthermore, it may be manufactured and/or used in preparation, i.e. manufacture or formulation, of a composition such as a medicament, pharmaceutical composition or drug. These may be administered to individuals for the treatment of cancer conditions as described below. Methods of the invention thus comprise formulating the test compound in a pharmaceutical composition with a pharmaceutically acceptable excipient, vehicle or carrier for therapeutic application, as discussed further below.

One example of such a compound is a gamma secretase inhibitor, which may be tested for activity against cell line-derived cancer stem cells within, or isolated from, cancer cell lines using methods that are available to one skilled in the art. Therefore, one embodiment of the invention is the evaluation of a gamma secretase inhibitor for anti-cancer activity by treating a cancer cell line with a gamma secretase inhibitor and specifically monitoring the effect on cell line-derived cancer stem cells (e.g., growth, cell death, anti-proliferation, differentiation status, etc.). This is accomplished using, for example, flow cytometry based on Hoechst dye exclusion, or using an antibody that specifically binds to the cell line-derived cancer stem cell population in combination with an apoptosis marker (e.g., Annexin, or Propidium Iodide).

Following identification of a compound, such as an antibody molecule, which inhibits the growth of cell line-derived cancer stem cells as described above, a method further comprises modifying the compound to optimise the pharmaceutical properties thereof. This modification may include conjugating the compound to a toxin, drug, prodrug, or radioisotope.

Further optimisation or modification can then be carried out to arrive at one or more final compounds for in vivo or clinical testing.

A compound which inhibits cancer stem cell growth, proliferation, and/or viability, or modulates cancer stem cell differentiation status or modulates the expression or activity of a cancer stem cell marker, as described above, may be formulated in a composition. A composition may include, in addition to the compound, a pharmaceutically acceptable excipient, carrier, buffer, stabiliser or one or more other materials well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, nasal, intramuscular, topical or intraperitoneal routes.

Pharmaceutical compositions for oral administration may be in tablet, capsule, powder or liquid form. A tablet may include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, cutaneous or subcutaneous injection, or injection at a particular site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

Another aspect of the invention provides a method of treatment of a cancer condition comprising;

administering a test compound identified as described herein, for example an antibody molecule which binds to a cancer stem cell, to an individual in need thereof.

A cancer condition may include lung cancer, gastrointestinal cancer, bowel cancer, colon cancer, breast carcinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma, lymphoma, retinoblastoma or leukaemia.

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of what is being treated. Prescription of treatment, e.g., decisions on dosage etc., is within the responsibility of general practitioners and other medical doctors, and typically takes account of the disorder to be treated, the condition of the individual patient, the site of delivery, the method of administration and other factors known to practitioners.

Examples of the techniques and protocols mentioned above can be found in Remington's Pharmaceutical Sciences, 16th edition, Osol, A. (ed), 1980.

Certain aspects and embodiments of the invention will now be illustrated by way of example and with reference to the accompanying Figures.

Examples

Materials and Methods

Chemicals.

Chemicals were purchased from Sigma unless otherwise indicated. Recombinant cytokines were purchased from PeproTech (Rocky Hill, N.J.) unless otherwise indicated.

Cell Culture

Various cancer cell lines were studied, including the rat glioma line C6, the human breast cancer line MCF-7, the human osteosarcoma lines U-20S and SaOS-2, the rat neuroblastomaline B104, and the human adenocarcinoma line HeLa.

The cells were cultured in DMEM, supplemented with 10% FCS, 100 units/ml penicillin G, and 100 μg/ml streptomycin (GIBCO). In some experiments, C6 cells were cultured in serum-free DMEM containing 10 μg/ml bovine insulin, 100 μg/ml human transferrin, 100 μg/ml BSA, 60 ng/ml progesterone, 16 μg/ml putrescine, 40 ng/ml sodium selenite, 63 μg/ml N-acetylcysteine, 5 μM forskolin, 50 units/ml penicillin, and 50 μg/ml streptomycin (GIBCO), as well as one or both of 10 ng/ml bFGF and 10 ng/ml PDGF, or one or both of bFGF (10 ng/ml) and EGF (10 ng/ml).

In all experiments, cells were maintained in 100-mm culture dishes (Nunc) or culture flasks (Iwaki Glass) at 37° C. in a humidified 5% $CO_2$/95% air atmosphere.

Flow Cytometry

To identify and isolate the SP cells in the cancer cell lines, the lines were cultured as described above, in either FCS or serum-free culture medium with bFGF, PDGF, or both. The cells were removed from the culture dish with trypsin and EDTA GIBCO BRL), washed, suspended at $10^6$ cells per ml in DMEM containing 2% FCS (staining medium), and preincubated in 1.5-ml Eppendorf tube at 37° C. for 10 min. The cells were then labeled in the same medium at 37° C. for 90 min with 2.5 μg/ml Hoechst 33342 dye (Molecular Probes), either alone or in combination with 50 μM verapamil (Sigma), which is an inhibitor of some (verapamil-sensitive) ABC transporters (Goodell, M. A. (1996) *J. Exp. Med.* 183 1797-1806.). Finally, the cells were counterstained with 1 μg/ml propidium iodide to label dead cells. Then, $3-5\times10^4$ cells were analyzed in a FACSVantage fluorescence-activated cell sorter (Becton Dickinson) by using dual-wavelength analysis (blue, 424-444 nm; red, 675 nm) after excitation with 350-nm UV light. Propidium iodide-positive dead cells (15%) were excluded from the analysis. In the case of the C6 cell line, the SP cells or non-SP cells were sorted and cultured in serum-free culture medium with bFGF and PDGF.

RNA Extraction and RT-PCR Assay

Cells were harvested, and poly(A)+RNA was prepared by using a QuickPrep Micro mRNA purification kit (Amersham Biosciences) and reverse transcribed by using a First-Strand cDNA synthesis kit (Amersham Biosciences), as described (Kondo, T. & Raff, M. (2000) *Science* 289, 1754-1757). The RT-PCR was carried out in a 20 μl reaction mixture that contained 1 μl of cDNA as template, 1 μM specific oligo-nucleotide primer pair, and 0.5 unit of Taq DNA polymerase (Takara Shuzo, Kyoto).

Cycle parameters for bcrp, mdr1, or g3pdh cDNAs were 30 sec at 94° C., 30 sec at 60° C., and 60 sec at 72° C. for 33, 32, and 25 cycles, respectively. The identity of the amplified products was checked by digestion with appropriate restriction enzymes. Oligonucleotide DNA primers were synthesized as follows. For rat bcrp, sequences conserved between human and mouse were used:

```
5'-CCAGTTCCATGGCACTGGCCATA-3'     (SEQ ID NO: 1)
and

5'-CAGGGCCACATGATTCTTCCACA-3'.    (SEQ ID NO: 2)
```

For rat mdr1, sequences conserved between human and mouse were used:

```
5'-GCAAAGCTGGAGAGATCCTCACCA-3'    (SEQ ID NO: 3)
and

5'-CAACATTTTCATTTCAACAACTCCTGC-3'. (SEQ ID NO: 4)
```

For rat g3pdh, the following sequences were used:

```
5'-ACCACAGTCCATGCCATCAC-3'        (SEQ ID NO: 5)
and

5'-TCCACCACCCTGTTGCTGTA-3'.       (SEQ ID NO: 6)
```

For other RT-PCR experiments, the following forward and reverse primers were used:

```
Notch 1:
5-AGCCTCAACATCCCCTACAAG-3         (SEQ ID NO: 7)
and

5-CAGTCGGCGTCAACCTCACC-3;         (SEQ ID NO: 8)

Notch 2:
5-AGAAACAGAGGATGACACGCAG-3        (SEQ ID NO: 9)
and

5-GCTTACGCTTTCGTTTTGCC-3;         (SEQ ID NO: 10)

Notch 3:
5-ATGGTGGAAGAGCTCATCGC-3          (SEQ ID NO: 11)
and

5-TGGCCTCCTGCTCTTCTTGG-3;         (SEQ ID NO: 12)

Notch 4:
5-TGTGGCTGCCCCCTGGTTTCA-3         (SEQ ID NO: 13)
and

5-GTGTCACCCCATCAGGTCCAC-3;        (SEQ ID NO: 14)

Hes1:
5-CCATGCCAGCTGATATAATGGAGAAAAA-3  (SEQ ID NO: 15)
and

5-AATCAGTTCCGCCACGGCCTCCA-3;      (SEQ ID NO: 16)

Hes3:
5-AGGTCTCTTCTGGAGAGACACT-3        (SEQ ID NO: 17)
and

5-CGCTGTCCGTGGTGCTGCCT-3;         (SEQ ID NO: 18)

Hes5:
5-CGACTGCGGAAGCCGGTGGT-3          (SEQ ID NO: 19)
and

5-AGCAGCTTCATCTGCGTGTCG-3         (SEQ ID NO: 20)
```

-continued frz1:
5-CGGGCAGCAGTACAACGGCGA-3 (SEQ ID NO: 21)
and

5-GTTCTGGCCCACGCACAGCTC-3; (SEQ ID NO: 22)

frz3:
5-GGAATATGGACGTGTCACACT-3 (SEQ ID NO: 23)
and

5-GCGAGCAAATGACAGTTCTTC-3; (SEQ ID NO: 24)

frz4:
5-TGAGACTAGTGGATGCCGATG-3 (SEQ ID NO: 25)
and

5-CCCTCTTCTCTCTCTTTACCTT-3; (SEQ ID NO: 26)

frz5:
5-CCAGGAAATCACGGTGCCCA-3 (SEQ ID NO: 27)
and

5-CGGTCGCAGCTCATGCGCTC-3; (SEQ ID NO: 28)

frz7:
5-ACACGAACCAAGAGGACGCG-3 (SEQ ID NO: 29)
and

5-GAGCCGTCGGACGTGTTCTG-3; (SEQ ID NO: 30)

wnt1:
5-GAGTGCAAATGCCACGGGATG-3 (SEQ ID NO: 31)
and

5-AGCTGACGTGGCAGCACCAG-3; (SEQ ID NO: 32)

wnt10:
5-CCGCTGACGGCCAACACCGT-3 (SEQ ID NO: 33)
and

5-ATCCCGAGAGAACTTCTCTCC-3; (SEQ ID NO: 34)

wnt11:
5-CTGATGCGTCTACACAACAG-3 (SEQ ID NO: 35)
and

5-GCAGAAGTCAGGGGAGCTCTG-3; (SEQ ID NO: 36)

gli1:
5-AGGGCAGCTCAAGGCTCAGC-3 (SEQ ID NO: 37)
and

5-TCATCTAGGATAGCCACAAAG-3; (SEQ ID NO: 38)

gli2:
5-CAGCAGAGGCTGTGCCCAAGG-3 (SEQ ID NO: 39)
and

5-GCGTGAGGAATTCTGGGAGA-3; (SEQ ID NO: 40)

gli3:
5-GTGGGCTTCAGTCAGCAAGAC-3 (SEQ ID NO: 41)
and

5-CTGCAAGGAACTTGCTTTCTT-3; (SEQ ID NO: 42)

Patch:
5-TCTGCTGGGTGTACTGATGC-3 (SEQ ID NO: 43)
and

5-AGAGTCCAGGTGGGGCTGTT-3; (SEQ ID NO: 44)

Smo:
5-CCTCCTGGTGGAGAAGATCAA-3 (SEQ ID NO: 45)
and

5-CTGGGGAGATCTCTGCCTCA-3; (SEQ ID NO: 46)

Shh:
5-GCCATCATTCAGAGGAGTCTC-3 (SEQ ID NO: 47)
and

5-CACGAAGAGCAGGTGCGCGG-3; (SEQ ID NO: 48)

hiwi:
5-CATCAATGAAGGGATGACCCG-3 (SEQ ID NO: 49)
and

5-TCTCACTGCCTGGCTCACGAT-3; (SEQ ID NO: 50)

Nucstem:
5-TTCCATGGGACTTACAAGGAG-3 (SEQ ID NO: 51)
and

5-AGGCACCTGTCCACTCAGACC-3; (SEQ ID NO: 52)

bmi1:
5-ATGCATCGAACAACCAGAAT-3 (SEQ ID NO: 53)
and

5-TCACTTTCCAGCTCTCCA-3; (SEQ ID NO: 54)

musashi1:
5-CCTGGTTACACCTACCAGTTC-3 (SEQ ID NO: 55)
and

5-TCAGTGGTACCCATTGGTGAAG-3; (SEQ ID NO: 56)

oct4:
5-CTGCTGAAGCAGAAGAGGATCAC-3 (SEQ ID NO: 57)
and

5-CTTCTGGCGCCGGTTACAGAACCA-3; (SEQ ID NO: 58)

prominin1:
5-AGGCTACTTTGAACATTATCTGCA-3 (SEQ ID NO: 59)
and

5-GGCTTGTCATAACAGGATTGT-3; (SEQ ID NO: 60)

integrin alpha-6:
5-GACTTCAGTTTCGAAACCAAG-3 (SEQ ID NO: 61)
and

5-GCCATTCTGGTTGGCAACACA-3; (SEQ ID NO: 62)

ER-alpha:
5-GCTGCCAACCTTTGGCCAAG-3 (SEQ ID NO: 63)
and

5-CCTTCTCTTCCAGAGACTTCA-3; (SEQ ID NO: 64)

ER-beta:
5-AAGAGGGATGCTCACTTCTGC-3 (SEQ ID NO: 65)
and

5-CCCTCATCCCTGTCCAGAAC-3; (SEQ ID NO: 66)

Mucin1(EMA):
5-GTACCATCAATGTCCACGAC-3 (SEQ ID NO: 67)
and

5-CTACGATCGGTACTGCTAGG-3; (SEQ ID NO: 68)

CK14:
5-GTGACCATGCAGAACCTCAA-3 (SEQ ID NO: 69)
and

5-TGCTGAGCTGGGACTGCAGCT-3; (SEQ ID NO: 70)

CK18:
5-AAGGTCATTGATGACACCAATA-3 (SEQ ID NO: 71)
and

5-GGATGGTTTGCATGGAGTTG-3; (SEQ ID NO: 72)
and

```
CK19:
5-GACAAGATTCTTGGTGCCAC-3         (SEQ ID NO: 73)
and

5-GACTGCAGCTCAATCTCAAG-3.        (SEQ ID NO:74)
```

Immunostaining of Cultured Cells

To examine the expression of neuronal, glial, and other stem cell markers in C6 and MCF-7 SP cells cultured for 1 or 10 days, the cells were cultured overnight in chamber slides (Nunc) precoated with 1 µg/ml fibronectin (Invitrogen) and 15 µg/ml ornithine (Sigma). The cells were fixed with 2% paraformaldehyde for 10 minutes at room temperature, treated with 20% FCS, and then stained with the following mouse monoclonal antibodies: anti-GFAP (1:200; Sigma), anti-β-III tubulin (1:200; Sigma), anti-microtubule-associated protein 2 (MAP2; 1:500; Sigma), anti-BCRP (1:100; Pharmingen), anti-CD133 (1:100; Pharmingen), rat monoclonal anti-Notch 1 (bTAN20; diluted 1:100, Developmental Studies Hybridoma Bank), rat monoclonal anti-Notch 2 (C651.6DbHN; diluted 1:100, Developmental Studies Hybridoma Bank) and anti-nestin (1:200; Pharmingen).

The primary antibodies were detected with Texas red-conjugated goat anti-mouse IgM or IgG (1:100; Jackson ImmunoResearch) as described (Kondo, T. & Raff, M. (2000) Science 289, 1754-1757), with the exception of the Notch antibodies, which were detected with primary antibodies were detected with Alexa-dye conjugated secondary antibodies (1:200, Molecular Probes). Also, antibodies specific for BCRP and CD133 were detected with FITC-conjugated goat anti-mouse IgG. The cells were counterstained with Hoechst 33342 to identify all nuclei. Immunoreactivity was determined by immunofluorescence microscopy.

Transplantation into Nude Mice

KSL_slc nude mice were purchased from SLC (Shizuoka, Japan). FACS-sorted C6 SP and non-SP cells were cultured for 7 days in bFGF plus PDGF, and $10^5$ cells of each type were injected i.p. into three 4-week-old female nude mice. The same experiment was repeated twice with similar results. The mice were killed 18 days after injection and examined for tumors, as described below. Mice were treated according to the guidelines of the Kumamoto University Animal Committee.

Hematocrit Analysis

Blood was collected in EDTA at a final concentration of 1 mM. Glass microcapillary tubes (Hirschmann) were filled with blood, capped with Parafilm, and centrifuged at 3,000×g for 1 minute, and the hematocrit was calculated as the proportion of the tube containing erythrocytes.

Immunostaining of Tissue Sections

Tumor-bearing tissues were fixed in 4% paraformaldehyde, embedded in Tissue-Tek OCT optimal cutting temperature) compound, and then frozen at 20° C. Cryostat sections (12 µm) were cut, mounted on poly-L-lysine-coated slides, and air-dried for 24 hours. To characterize the cells in tumors, the sections were treated with 10% normal goat serum (DAKO) for 30 minutes at room temperature and then stained with the following mouse monoclonal antibodies: antinestin antibody, anti-GFAP antibody, and anti-low molecular weight neurofilament antibody (1:200; Sigma). The primary antibodies were detected with Alexa 594-conjugated goat antimouse IgG (1:200; Molecular Probes). The cells were counterstained with Hoechst 33342 to identify all nuclei. The stained sections were examined and photographed in an AX70 fluorescence microscope (Olympus, Orangeburg, N.Y.).

Treatment of Cell Lines with Gamma Secretase Inhibitor

MCF-7 cells were cultured in serum-containing media, as described above. Cells were harvested from the cultures, washed, and resuspended in gamma secretase inhibitor I. Gamma secretase inhibitor I was purchased from Calbiochem™ (San Diego, Calif.; Catalog number 565750). The gamma secretase inhibitor was added to the cultures at a final concentration of 1 uM. Cells were treated for 7 days, and the SP was quantitated as described.

Results

Many Cancer Cell Lines Contain a Small SP

To determine whether any of the six established cancer cell lines in our collection contained SP cells, cells were removed from the culture dishes with trypsin and EDTA and stained with the fluorescent dye Hoechst 33342, which has been shown to be extruded actively by the SP cells in various tissues by means of verapamil-sensitive ABC transporters. They were then analyzed by flow cytometry. As shown in FIG. 1, the C6 glioma cells contained 0.4% SP cells (FIG. 1A), the MCF7 breast cancer cells contained 2.0% SP cells (FIG. 1B), the B104 neuroblastoma cells contained 0.4% SP cells (FIG. 1C), and the HeLa carcinoma cells contained 1.2% SP cells (FIG. 1D). In each case, the SP was decreased greatly by treatment with verapamil, indicating that the populations were bona fide SPs (see FIG. 1E-H). Thus, some cancer cell lines contain a small SP, despite having been maintained in culture for many years. No SP cells were detected in the two human osteosarcoma lines (U-20S and SaOS-2).

C6 SP Cells can be Expanded in bFGF Plus PDGF.

PDGF is the main mitogen for oligodendrocyte precursor cells (Noble, M. et al (1988) Nature 333, 560-562.), whereas bFGF is a major mitogen for NSCs (Nurcombe, V. et al (1993) Science 260, 103-106). Unfractionated C6 cells were cultured on uncoated dishes in 10% FCS or in serum-free culture medium with PDGF, bFGF, or both.

The morphology of the cells was found to be very different in the different culture conditions. In FCS or bFGF alone, the cells had a flat, fibroblast-like shape. In PDGF, they had a round body but were still attached to the dish. In the presence of both after 10 days, just as CNS NSCs do under similar conditions (Chiasson, B. J. et al (1999) J. Neurosci. 19, 4462-4471).

Figure 2:
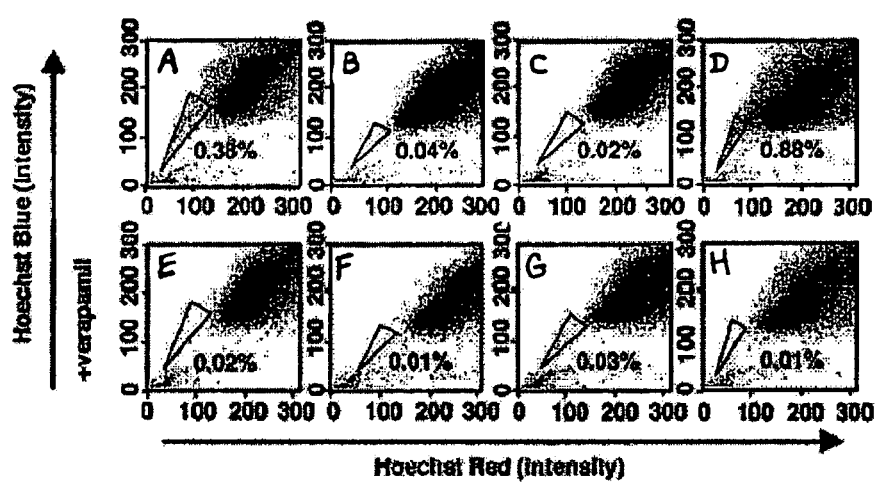
FIG. 2A-2H shows the roles of PDGF and bFGF on C6 SP cells. C6 SP cells were cultured for 3 weeks in FCS (A, E) or serum-free medium with bFGF (B, F), PDGF (C, G), or both (D, H) and were analyzed by flow cytometry as shown in FIG. 1. (E-H) Results when the cells were treated with 50-μM verapamil during the labeling procedure. All experiments were repeated at least three times with similar results.
Figure 3:
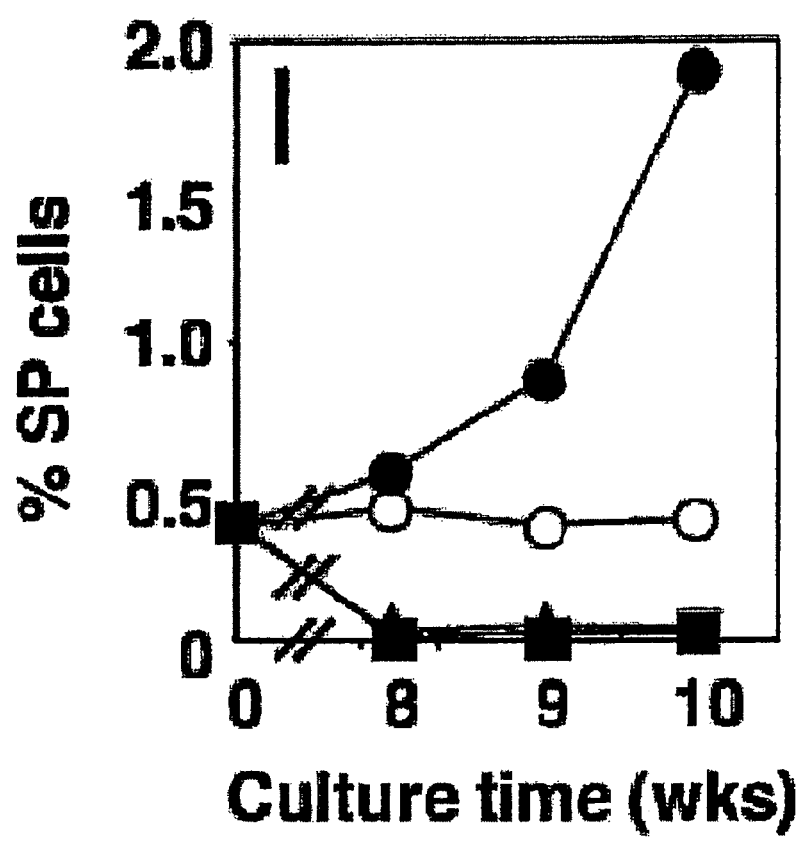
FIG. 3 shows the roles of PDGF and bFGF on C6 SP cells. C6 cells were cultured in FCS (open circle), bFGF (closed triangle), PDGF (closed square), or bFGF plus PDGF (closed circle) for the indicated times, and the proportion of SP cells was analyzed by flow cytometry. All experiments were repeated at least three times with similar results.

The cells were stained with Hoechst 33342 and analyzed by flow cytometry. When cultured in serum-free medium with both PDGF and bFGF, SP cells were maintained, and their proportion increased with time (FIGS. 2 and 3). By contrast, when cultured in either bFGF or PDGF alone, the C6 cells survived and proliferated, but by 3 weeks few SP cells could be detected (FIGS. 2 and 3). These findings indicate that C6 SP cells can expand in a combination of bFGF and PDGF but cannot be maintained in either growth factor alone.

The expression of bcrp mRNA, which encodes a verapamil sensitive ABC transporter, as well as mdr1 mRNA, which encodes another ABC transporter, was examined in C6 cells cultured in the four conditions described above.

bcrp mRNA expression was detected in the presence of both PDGF and bFGF but not in FCS or in bFGF or PDGF alone. In contrast, mdr1 mRNA was expressed in FCS, bFGF, or bFGF plus PDGF, although it was not expressed in PDGF alone. Together, these data indicate that BCRP, but not MDR1, is responsible for the SP character of some C6 cells.

Figure 4:
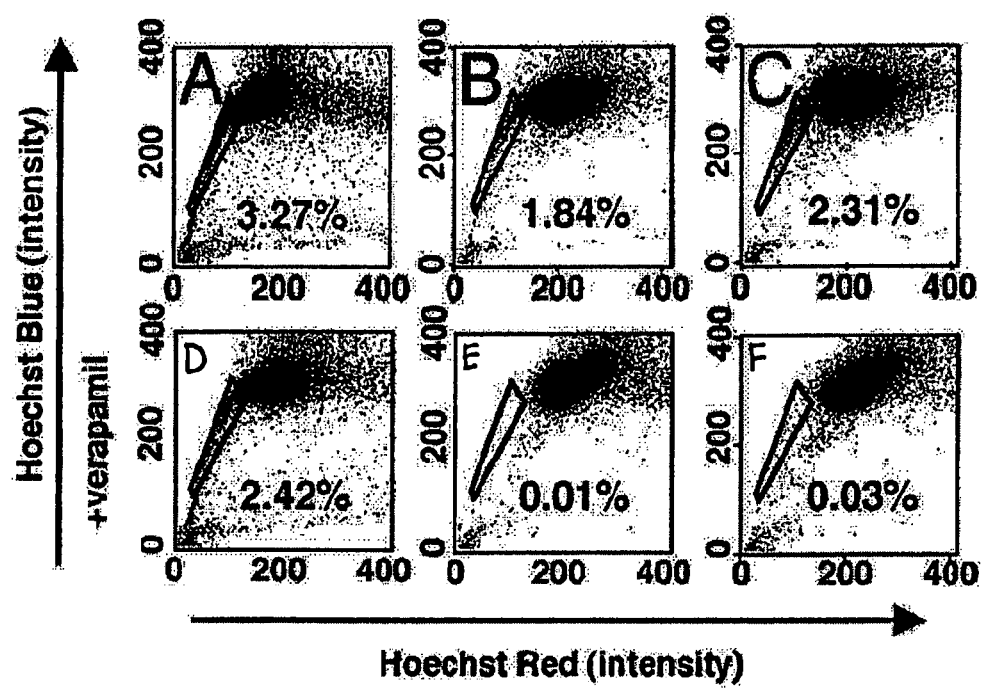
FIG. 4A-4F shows the different roles of bFGF and PDGF on C6 SP cells. C6 cells were cultured in PDGF (A, D), bFGF (B, E), or both (C, F) for 2 weeks and then expanded in bFGF plus PDGF for an additional 2 weeks in the presence (D-F) or absence (A-C) of verapamil. They were then analyzed by flow cytometry as described for FIG. 1. All experiments were repeated at least three times with similar results.

To investigate the individual roles of PDGF and bFGF in expanding C6 SP cells, C6 cells were cultured in either bFGF or PDGF for 2 weeks and then in bFGF plus PDGF for an additional 2 weeks. The cells were then stained with Hoechst 33342 and analyzed by flow cytometry. As shown in FIG. 4, 1.8% of the cells cultured in bFGF and then in bFGF plus PDGF were SP cells. By contrast, although there seemed to be SP cells after culturing in PDGF and then in bFGF plus PDGF, these cells were still seen when stained in the presence of verapamil (FIG. 4), indicating that they were not bona fide SP cells. The expression of both bcrp and mdr1 mRNA in C6 cells cultured was also examined under these two conditions. As shown in FIG. 4 D, bcrp mRNA was detected in the cells that were cultured in bFGF and then in PDGF plus bFGF, but not in the cells cultured in PDGF and then in PDGF plus bFGF; by contrast, mdr1 mRNA was detected in both conditions. It is possible, therefore, that bFGF on its own maintains C6 SP cells at an undetectable low level and that PDGF stimulates the proliferation of these cells.

Figure 7:
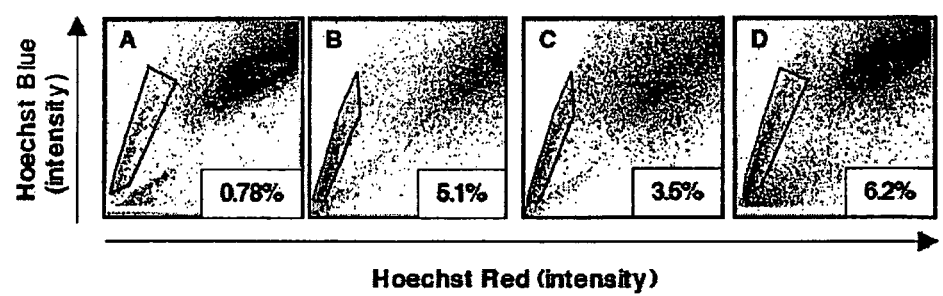
FIG. 7A-7D shows the roles of EGF and bFGF on MCF7 SP cells. The cells were cultured in FCS (A) or serum-free medium with bFGF (B), EGF (C), or both (D) for 7 days and were analyzed by flow cytometry. The SP is outlined and shown as a % of the total cell population.

MCF7 Cell Expansion MCF7 cells were cultured in 10% FCS (FIG. 7A) or in serum-free culture medium with bFGF (FIG. 7B), EGF (FIG. 7C), or both (FIG. 7D) for 7 days. In FCS, the cells had a flat and fibroblast-like shape, however, in the serum-free medium, they formed floating aggregates, known as mammospheres (Dontu, G. et al (2003) Genes Dev. 17, 1253-1270.). Cells were stained with Hoechst dye and analyzed by flow cytometry. When cultured in FCS, less than 0.8% of the cells are SP cells. By contrast, when cultured in serum-free medium with bFGF, EGF or both, 5.1%, 3.5%, or 6.2% of the cells, respectively, are SP cells. This indicates that MCF7 SP cells significantly expand in serum-free medium supplemented with bFGF and EGF.

C6 SP Cells can Repopulate Both SP and Non-SP C6 Cells.

Figure 5:
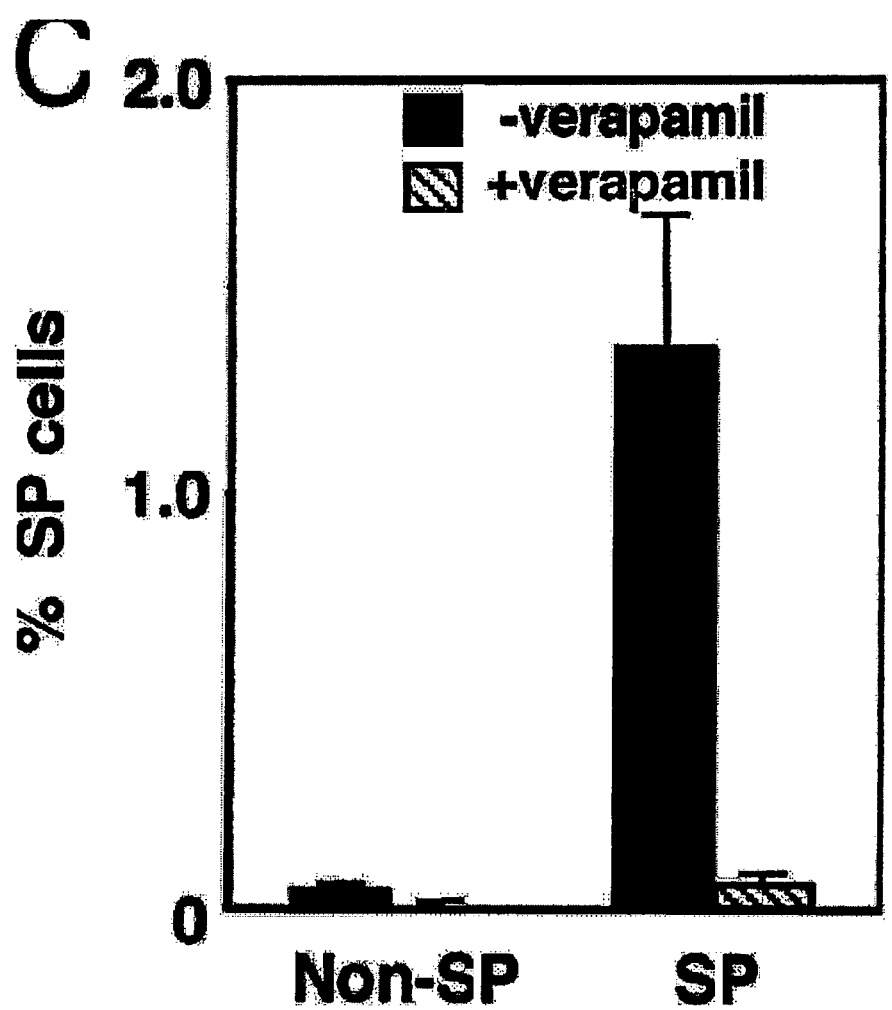
FIG. 5 shows that SP cells in the C6 glioma cell line can generate both SP and non-SP C6 cells. C6 cells were cultured in bFGF plus PDGF for 2 weeks and then sorted by flow cytometry as described for FIG. 1. The SP and non-SP cells were then cultured separately in the same conditions for an additional 2 weeks. The cells were then analyzed by flow cytometry as shown in FIG. 1.

To compare the ability of C6 SP cells with the ability of non-SP cells to produce SP cells, C6 cells were cultured without FCS and in PDGF plus bFGF for 2 weeks, stained with Hoechst 33342, and sorted into SP and non-SP fractions by flow cytometry. The SP and non-SP cells were then expanded separately in the same medium for an additional 2 weeks. As they proliferated, the cells in the two populations had different morphologies. The cells in the SP cultures formed floating spheres, whereas the cells in the non-SP cultures remained attached to the culture dishes and had a fibroblast-like morphology. When the cells were re-stained with Hoechst 33342 and re-analyzed by flow cytometry, it was found that the cultures initiated with SP cells contained both SP and non-SP cells, whereas the cultures initiated with non-SP cells contained only non-SP cells (FIG. 5).

These data are consistent with previous findings that only the SP cells in primary neurospheres can produce both SP and non-SP cells in culture (Hulspas, R. & Quesenberry, P. J. (2000) *Cytometry* 40, 245-250). Furthermore, when single FACS-sorted SP cells were cultured alone in the same medium in a well of a 98-well culture plate, 70% of the cells proliferated and reformed floating spheres; in contrast, single non-SP cells cultured in the same way proliferated much more slowly, and almost all of the cells died by 3 weeks. Thus, C6 SP cells, but not non-SP cells, can form floating spheres, proliferate extensively, and produce C6 SP cells in culture.

C6 SP Cells can Produce Both Neurons and Glia in Culture

SP cells were sorted, cultured for 1 or 10 days in PDGF plus bFGF on ornithine-fibronectin-coated chamber slides, and then immunolabeled for neuronal and glial markers. After 1 day, 90% of the cells were labeled for the NSC marker nestin (92+/−2%), but none were labeled for the neuronal markers MAP2 or β-III tubulin or the astrocyte marker GFAP, suggesting that C6 SP cells might be undifferentiated NSC-like cells. After 10 days, however, 70% were immunolabeled for β-III tubulin, 5% for MAP2, and 7% for GFAP. Thus, C6 SP cells can generate both neurons and glial cells in culture.

The Malignancy of C6 Cells In Vivo is Largely Dependent on the SP Cells

To address whether SP and non-SP C6 cells differ in their malignancy, C6 cells growing in PDGF plus bFGF were sorted into SP and non-SP cells, expanded in the same medium for 1 week, and then $10^5$ cells from either population were injected i.p. into nude mice.

Figure 6:
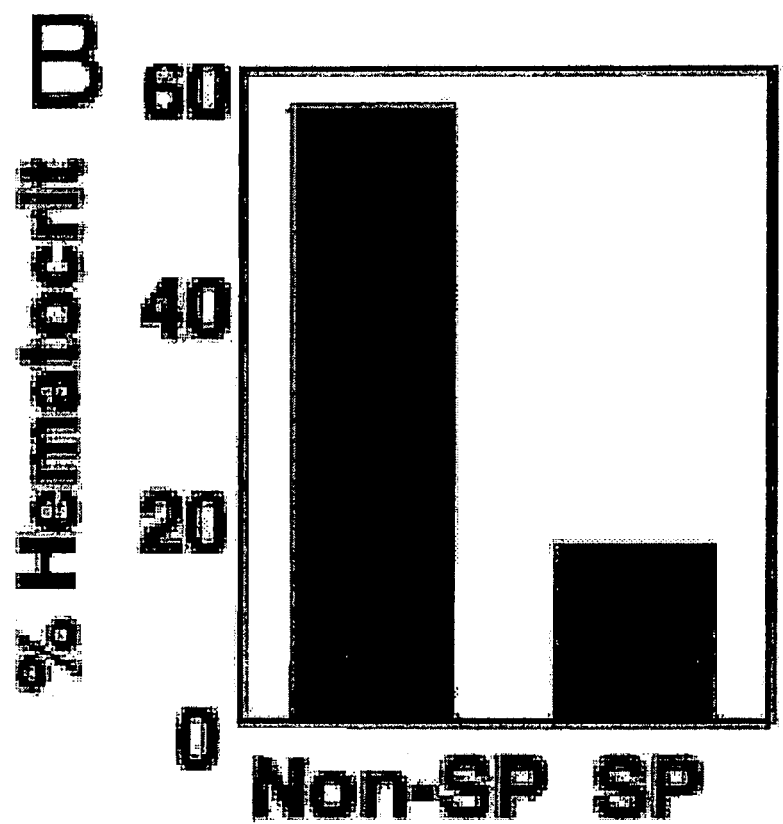
FIG. 6 shows evidence of malignancy of C6 SP cells in vivo. SP or non-SP C6 cells ($10^5$) were injected i.p. into 4-week-old female nude mice. The mice were killed 18 d later and the hematocrit was measured.

After 18 days, all mice injected with cells from the SP cultures showed intraabdominal hemorrhages (FIG. 6) and tumor invasion into the mesentery, uterus and lymph nodes. In four of six mice, there was also tumor invasion into the lungs. In contrast, after the same period, the cells from non-SP cultures had not formed tumors that invaded into these tissues, although we detected one s.c. tumor and an occasional small metastasis in mesenteric lymph nodes.

Thus, much of the malignancy of the C6 line depends on SP cells. To determine whether C6 cells could produce neurons and glia in vivo, the tumor-bearing tissues were fixed in 4% paraformaldehyde, and frozen sections cut and immunolabeled for neuronal and glial markers.

35% of the cells in the tumors were immunolabeled for nestin, 30% for GFAP, and 15% for the neuronal marker NF-L (low molecular weight neurofilament), indicating that C6 SP cells can differentiate into both neurons and glia in vivo.

Figure 9:
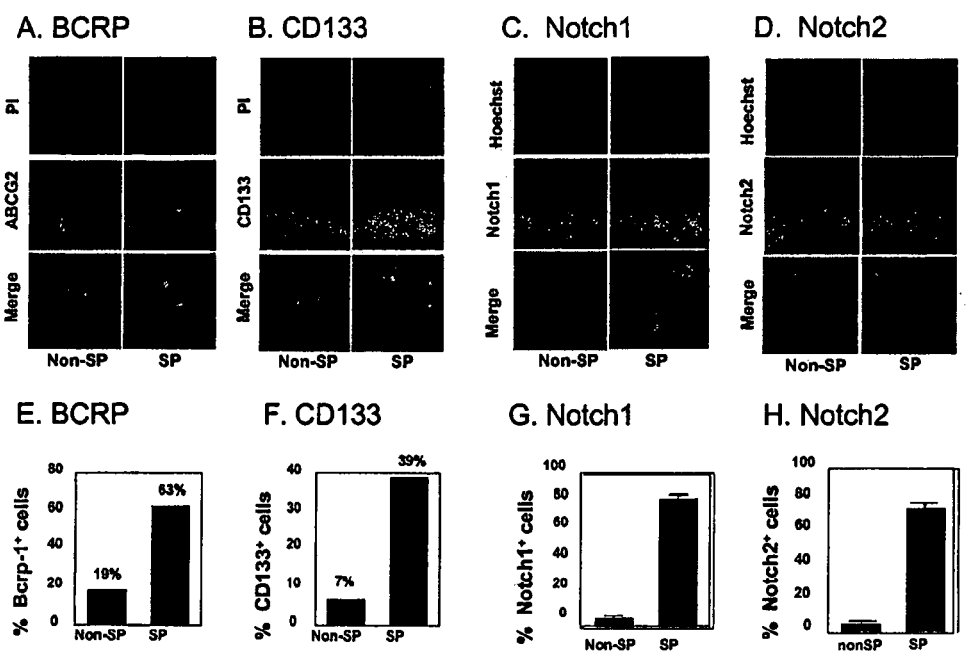
FIG. 9A-9H shows that cancer stem cells within the cancer cell line MCF-7 can be identified using monoclonal antibodies specific for cell surface proteins. SP and non-SP cells were isolated by flow cytometry. Cells were fixed in paraformaldehyde and incubated with fluorescently-labeled antibodies that specifically bind to BCRP (panel A), CD133 (panel B), Notch 1 (panel C), and Notch 2 (panel D). Antibody staining was determined by immunofluorescence microscopy, and the percentage of positive cells in each population was quantitated (panels E-H).

Identification of Cell Line-Derived Cancer Stem Cells by Binding of Monoclonal Antibodies In cancer cell lines, cell line-derived cancer stem cells can also be identified using monoclonal antibodies that specifically bind to surface proteins. SP and non-SP cells were isolated by flow cytometry, spun onto chamber slides, and fixed, as described above. Cells were then incubated with fluorescently-labeled antibodies specific for BCRP (FIG. 9A), CD133 (FIG. 9B), Notch 1 (FIG. 9C), and Notch 2 (FIG. 9D). Nuclei were counterstained with propidium iodide or Hoechst 33342, as indicated. The percentage of cells from each population that were bound by the antibodies was quantitated using fluorescence microscopy, with a minimum of 1000 total cells counted for each population. The results demonstrate that each of the antibodies tested binds to the majority of SP cells, and not the non-SP cell population, as shown in FIGS. 9E-H. Therefore, Hoechst staining or antibodies can be used to specifically recognize cell line-derived cancer stem cells.

Figure 8:
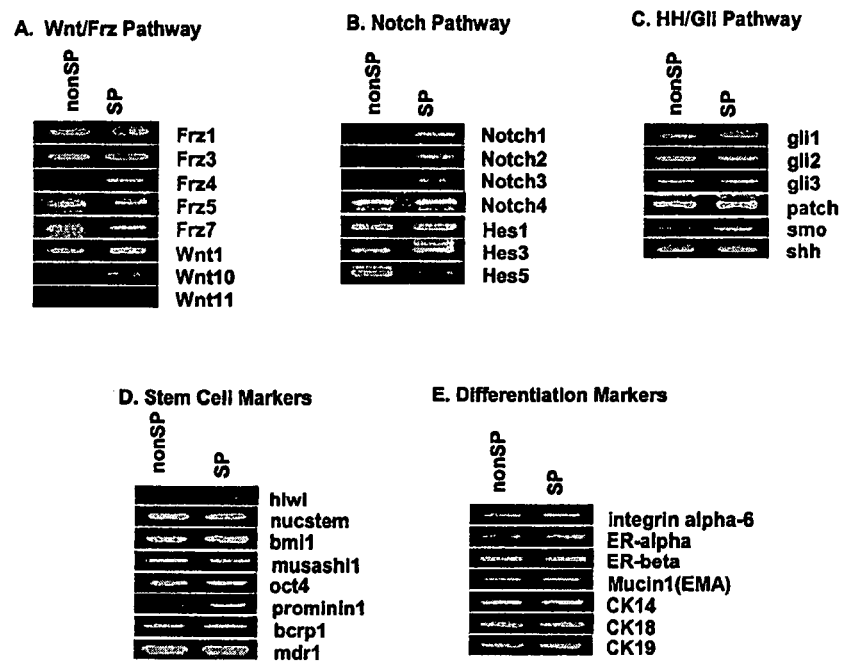
FIG. 8A-8E shows the results of a comparative study of the gene expression profiles of cancer stem cells and non-cancer stem cells of the human breast cancer cell line, MCF-7, and identifies gene products that are differentially expressed by cancer stem cells. SP and non-SP cells were isolated as described above, and RNA was prepared as described. Expression of genes associated with the Wnt, Notch, and Hedgehog (HH) pathways, as well as a variety of stem cell and differentiation markers, was assessed by RT-PCR using gene specific primers.

Analysis of Gene Expression of Cancer Stem Cell Markers in Cell Line-Derived Cancer Stem Cells In another embodiment of the invention, cell line-derived cancer stem cells can be isolated from cancer cell lines using gene expression analysis. SP and non-SP cell were isolated from the MCF-7 breast cancer cell line. RNA was then isolated using standard protocols. Certain families of genes were selected for analysis based on their role in cancer biology, or their known function in normal stem cells. These families include the molecules involved in the Wnt pathway, the Notch pathway, and the Hedgehog (HH) pathway. Also, genes for various stem cell and differentiation markers were also tested. Primers were designed based on the sequences of these genes as set forth above, and RT-PCR was performed. Results indicate that Wnt10, Wnt11, Notch 1 Notch 2, Notch 3, and prominin-1 have increased expression in the SP cells relative to non-SP cells (see FIG. 8). These data can be readily used to design promoter-reporter constructs to be employed in drug screens to discover anti-cancer stem cell compounds. For example, the promoter of the Wnt10 gene could be fused with the gene encoding green fluorescent protein (GFP) to create a chimeric gene that specifically expresses GFP in the cell line-derived cancer stem cell population of MCF-7. Compounds can be tested for activity using the GFP-transfected cell line, and cell line-derived cancer stem cell death can be measured using fluorescently-labeled markers of apoptosis, such as Annexin.

Treatment of Cell Lines with Gamma Secretase Inhibitor I

Figure 10:
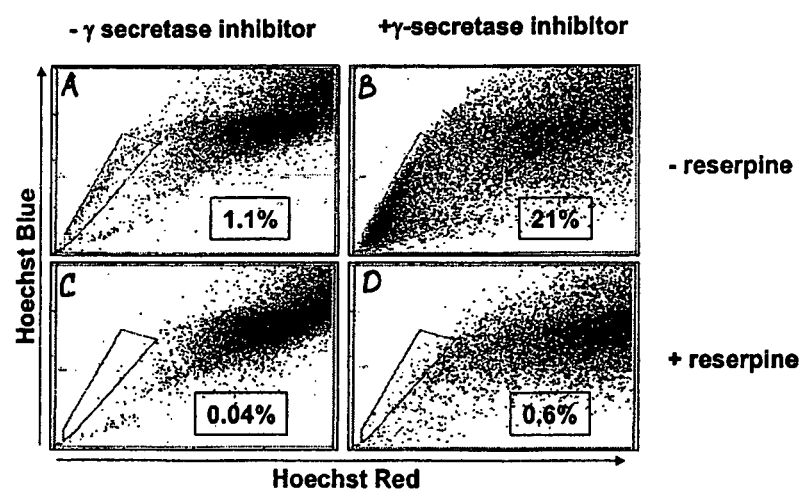
FIG. 10A-10D illustrates the results of a screen for anti-cancer stem cell activity using the MCF-7 cancer cell line. MCF-7 cells were incubated with 1 uM gamma secretase inhibitor (Calbiochem, San Diego, catalog number 565750) for 7 days (B, D). Control cells were cultured without a gamma secretase inhibitor (A, C). Following drug treatment, cells were washed, and then the SP was analyzed as described herein, in the presence (C, D) or absence (A, B) of 10 uM reserpine. The percentage of SP cells in the culture is given for each experimental condition.

The invention includes methods for evaluating compounds for anti-cancer stem cell activity by monitoring the SP cell population of a cancer cell line. In this experiment, MCF-7 cells were treated with a gamma secretase inhibitor, as described above. The Notch pathway has been shown to promote the self-renewal of stem cells, and gamma secretase activates this pathway by cleaving the Notch protein (De Strooper et al., Nature 398: 518-522 (1999), Mumm et al., Molecular Cell. 5: 197-206 (2000)). Therefore, gamma secretase inhibitors could affect cancer stem cells expressing the Notch protein. FIG. 10 shows that MCF-7 cells treated with 1 uM gamma secretase inhibitor for 7 days results in the expansion of the SP cell population from 1.1% to 21%. As expected, in the presence of reserpine, BCRP is inhibited, and no SP is visible. As described above, the SP corresponds with the cancer stem cells within a cell line. Therefore, these results validate the method of monitoring the SP cell population fate, whether positive or negative, in cancer cell lines while screening compounds for potential anti-cancer stem cell activity. While it was expected that a gamma secretase inhibitor might decrease the SP, instead this assay demonstrated that under these conditions, this gamma secretase inhibitor caused an increase in the SP. These findings indicate that gamma-secretase inhibitors can differentially affect SP versus non-SP cells. Given that Notch has been described as both a tumor suppressor and an oncogene, and that Notch is a target of gamma-secretase inhibitors, then treatment of a cancer cell line with a gamma secretase inhibitor may ultimately affect different cellular phenotype outcomes (Nature Reviews Cancer 3: 756-767 (2003)), This demonstrates that a gamma-secretase inhibitor such as the one described herein may either increase SP or decrease SP depending on the activity of Notch in any given system. Thus, the differential effect on SP versus non-SP cells by the gamma secretase inhibitor (FIG. 10) indicates that certain gamma secretase inhibitors may negatively affect cancer stem cells in certain contexts, while others of this class may not under the same conditions. In addition, compounds of other classes, not necessarily inhibiting gamma-secretase, are expected by these results to differentially affect the SP and in certain cases have a negative effect on SP—an effect that can be readily identified through these same screening methods.

CONCLUSION

The above described findings illustrate that cancer stem cells may be present in cancer cell lines in culture, even when the cell lines have been maintained for many years. An SP was detected in four of the six cancer cell lines tested, and in most normal tissues, the stem cells are found in the SP. In addition, cell line-derived cancer stem cells can also be detected using antibodies to cell surface markers. In the MCF-7 cell line, BCRP, CD133, Notch 1, and Notch 2 were differentially expressed by the SP cell population, and therefore each can be used to identify cell line-derived cancer stem cells in this cell line. Also, these results demonstrate that gene products that are differentially expressed in cell line-derived cancer stem cells can also be identified by RT-PCR. This includes cell surface proteins as well as intracellular proteins. The promoters of genes differentially expressed by cell line-derived cancer stem cells can be used to create promoter-reporter constructs in order to force the expression of detectable proteins, such as green fluorescent protein or luciferase, that enable the identification of the cell line-derived cancer stem cell population within the cell line. As taught by the invention, each of these strategies enables the use of cancer cell lines in drug screens, including high throughput screens, and in the testing of compounds identified using these screens, for anti-cancer stem cell activity.

The SP of the C6 glioma line, which comprises only 0.4% of the cells maintained in serum, has a number of characteristics that are expected of cancer stem cells. The SP cells in culture can self-renew and produce both SP and non-SP C6 cells, whereas the non-SP cells under the same culture conditions can produce non-SP cells only. Also, the C6 SP cells in culture can form neurospheres and produce neurons as well as glial cells, indicating that they have normal stem cell-like properties. Finally, the C6 SP cells produce tumors in nude mice with high efficiency, whereas the non-SP C6 cells do not.

In summary, the present invention illustrates the importance of cell line-derived cancer stem cells and provide methods for isolating them. The invention also illustrates that cancer cell lines are important models for studying the basic biology of stem cells. The invention further provides methods for using cancer cell lines as a source of cancer stem cells to evaluate test compounds for anti-cancer stem cell activity in drug screens, including high throughput screens. In addition, the invention teaches the development and use of assays that enable the testing of compounds for anti-cancer stem cell activity. The invention also provides methods for using cancer stem cells isolated from cell lines in the testing of compounds for anti-cancer stem cell activity.

The invention claimed is:

1. A method for the identification of a compound that inhibits the growth, viability, and/or proliferation of cell line-derived cancer stem cells in a cancer cell line comprising (i) contacting the cancer cell line with one or more test compounds, wherein the cancer cell line comprises cell line-derived cancer stem cells and tumor bulk; (ii) determining the effect of the one or more test compounds on the growth, viability, and/or proliferation of cell line-derived cancer stem cells in the cancer cell line and determining the effect of the one or more test compounds on the growth, viability and/or proliferation of cells from the tumor bulk in the cancer cell line; and (iii) comparing the effect of the one or more test compounds on the growth, viability, and/or proliferation of cell line-derived cancer stem cells in the cancer cell line with the effect of the one or more test compounds on the growth, viability, and/or proliferation of cells from the tumor bulk in the cancer cell line, wherein a test compound is identified as a compound that inhibits the growth, viability, and/or proliferation of cell line-derived cancer stem cells if it: (a) inhibits the growth, viability, and/or proliferation of the cell line-derived cancer stem cells in the cancer cell line but does not inhibit the growth, viability, and/or proliferation of cells from the tumor bulk in the cancer cell line or (b) inhibits the growth, viability, and/or proliferation of the cell line-derived cancer stem cells in the cancer cell line and also inhibits the growth, viability, and/or proliferation of cells from the tumor bulk in the cancer cell line, wherein the cell line comprises a detectable reporter that is specifically expressed by the cell line-derived cancer stem cells and not by the cells from the tumor bulk in the cancer cell line, wherein the effect of the one or more test compounds on the growth, viability, and/or proliferation of the cell line-derived cancer stem cells and cells from the tumor bulk in the cancer cell line is determined by monitoring the expression or activity of the detectable reporter; and wherein the tumor bulk comprises cells that are not cell line-derived cancer stem cells.

2. The method of claim 1, wherein the growth, viability, and/or proliferation of the cell line-derived cancer stem cells is monitored using a detectable marker for cell death, proliferation, and/or differentiation.

3. The method of claim 2, wherein the detectable marker is Annexin or propidium iodide.

4. The method of claim 1, wherein the effect of the one or more test compounds on the growth, viability, and/or proliferation of the cell line-derived cancer stem cells and tumor bulk is determined by monitoring the binding of the compound to the cell line-derived cancer stem cells.

5. The method of claim 1, the effect of the one or more test compounds on the growth, viability, and/or proliferation of the cell line-derived cancer stem cells and tumor bulk is determined by monitoring the expression or activity of one or more cell line-derived cancer stem cell markers.

6. The method of claim 1, wherein the effect of the one or more test compounds on the growth, viability, and/or proliferation of the cell line-derived cancer stem cells and tumor bulk is determined by monitoring the morphology of the cell line-derived cancer stem cells.

7. The method of claim 1, wherein the method is a high throughput method.

8. The method of claim 1, wherein a gene for the detectable reporter is linked to a promoter.

9. The method of claim 1, wherein the detectable reporter is a fluorescent reporter.

10. The method of claim 9, wherein the detectable reporter is green fluorescent protein (GFP) or luciferase.

11. The method of claim 1, wherein the effect of the one or more test compounds on the growth, viability and/or proliferation of the cell line-derived cancer stem cells and tumor bulk is determined using at least one of the following techniques: flow cytometry, fluorimetry, microscopy, immunofluorescence, ELISA, radioimmunoassay, immunoenzymatic assay, fluorescence activated cell sorting (FACS), PCR, RT-PCR, differential display, representational difference analysis, microarray, suppressive subtractive hybridization, direct sequencing, Western blotting, immunohistochemical staining, and immunocytochemical staining.

12. The method of claim 1, wherein the cell-line is a human cell line.

13. The method of any one of claim 1, wherein the cell-line is one of the following: HeLa cells, MCF-7 cells, C6 cells, or B104 cells.

14. The method of claim 1, wherein the cell-line is a prostate cancer cell line, an adenocarcinoma cell line, a lung cancer cell line, a gastrointestinal cancer cell line, a colon cancer cell line, a breast carcinoma cell line, an ovarian carcinoma cell line, a testicular cancer cell line, a glioma cell line, a liver cancer cell line, a kidney cancer cell line, a bladder cancer cell line, a pancreatic cancer cell line, a brain cancer cell line, a neuroblastoma cell line, a sarcoma cell line, an osteosarcoma cell line, a melanoma cell line, a lymphoma cell line, a retinoblastoma cell line, a skin cancer cell line, or a leukemia cell line.

15. The method of claim 14, wherein the breast carcinoma cell line is an MCF-7 cell line that comprises a gene for a detectable reporter that is linked to a promoter of a gene that is expressed in MCF-7 derived cancer stem cells, and wherein said detectable reporter is green fluorescent protein (GFP).

16. The method of claim 1, wherein said cell line-derived cancer stem cells can establish a tumor in vivo.

* * * * *

SEQUENCE LISTING

```
<160> NUMBER OF SEQ ID NOS: 74

<210> SEQ ID NO 1
<211> LENGTH: 23
<212> TYPE: DNA
<213> ORGANISM: Artificial Sequence
<220> FEATURE:
<223> OTHER INFORMATION: Rat bcrp forward primer

<400> SEQUENCE: 1
```

```
ccagttccat ggcactggcc ata                                              23

<210> SEQ ID NO 2
<211> LENGTH: 23
<212> TYPE: DNA
<213> ORGANISM: Artificial Sequence
<220> FEATURE:
<223> OTHER INFORMATION: Rat bcrp reverse primer

<400> SEQUENCE: 2
cagggccaca tgattcttcc aca                                              23

<210> SEQ ID NO 3
<211> LENGTH: 24
<212> TYPE: DNA
<213> ORGANISM: Artificial Sequence
<220> FEATURE:
<223> OTHER INFORMATION: Rat mdr1 forward primer

<400> SEQUENCE: 3
gcaaagctgg agagatcctc acca                                             24

<210> SEQ ID NO 4
<211> LENGTH: 27
<212> TYPE: DNA
<213> ORGANISM: Artificial Sequence
<220> FEATURE:
<223> OTHER INFORMATION: Rat mdr1 reverse primer

<400> SEQUENCE: 4
caacattttc atttcaacaa ctcctgc                                          27

<210> SEQ ID NO 5
<211> LENGTH: 20
<212> TYPE: DNA
<213> ORGANISM: Artificial Sequence
<220> FEATURE:
<223> OTHER INFORMATION: Rat g3pdh forward primer

<400> SEQUENCE: 5
accacagtcc atgccatcac                                                  20

<210> SEQ ID NO 6
<211> LENGTH: 20
<212> TYPE: DNA
<213> ORGANISM: Artificial Sequence
<220> FEATURE:
<223> OTHER INFORMATION: Rat g3pdh reverse primer

<400> SEQUENCE: 6
tccaccaccc tgttgctgta                                                  20

<210> SEQ ID NO 7
<211> LENGTH: 21
<212> TYPE: DNA
<213> ORGANISM: Artificial Sequence
<220> FEATURE:
<223> OTHER INFORMATION: Notch 1 forward primer

<400> SEQUENCE: 7
agcctcaaca tccctacaa g                                                 21

<210> SEQ ID NO 8
<211> LENGTH: 20
<212> TYPE: DNA
```

```
<213> ORGANISM: Artificial Sequence
<220> FEATURE:
<223> OTHER INFORMATION: Notch 1 reverse primer

<400> SEQUENCE: 8
cagtcggcgt caacctcacc                                              20

<210> SEQ ID NO 9
<211> LENGTH: 22
<212> TYPE: DNA
<213> ORGANISM: Artificial Sequence
<220> FEATURE:
<223> OTHER INFORMATION: Notch 2 forward primer

<400> SEQUENCE: 9
agaaacagag gatgacacgc ag                                           22

<210> SEQ ID NO 10
<211> LENGTH: 20
<212> TYPE: DNA
<213> ORGANISM: Artificial Sequence
<220> FEATURE:
<223> OTHER INFORMATION: Notch 2 reverse primer

<400> SEQUENCE: 10
gcttacgctt tcgttttgcc                                              20

<210> SEQ ID NO 11
<211> LENGTH: 20
<212> TYPE: DNA
<213> ORGANISM: Artificial Sequence
<220> FEATURE:
<223> OTHER INFORMATION: Notch 3 forward primer

<400> SEQUENCE: 11
atggtggaag agctcatcgc                                              20

<210> SEQ ID NO 12
<211> LENGTH: 20
<212> TYPE: DNA
<213> ORGANISM: Artificial Sequence
<220> FEATURE:
<223> OTHER INFORMATION: Notch 3 reverse primer

<400> SEQUENCE: 12
tggcctcctg ctcttcttgg                                              20

<210> SEQ ID NO 13
<211> LENGTH: 21
<212> TYPE: DNA
<213> ORGANISM: Artificial Sequence
<220> FEATURE:
<223> OTHER INFORMATION: Notch 4 forward primer

<400> SEQUENCE: 13
tgtggctgcc ccctggtttc a                                            21

<210> SEQ ID NO 14
<211> LENGTH: 21
<212> TYPE: DNA
<213> ORGANISM: Artificial Sequence
<220> FEATURE:
<223> OTHER INFORMATION: Notch 4 reverse primer

<400> SEQUENCE: 14
gtgtcacccc atcaggtcca c                                            21
```

<210> SEQ ID NO 15
<211> LENGTH: 28
<212> TYPE: DNA
<213> ORGANISM: Artificial Sequence
<220> FEATURE:
<223> OTHER INFORMATION: Hes1 forward primer

<400> SEQUENCE: 15
ccatgccagc tgatataatg gagaaaaa                                28

<210> SEQ ID NO 16
<211> LENGTH: 23
<212> TYPE: DNA
<213> ORGANISM: Artificial Sequence
<220> FEATURE:
<223> OTHER INFORMATION: Hes1 reverse primer

<400> SEQUENCE: 16
aatcagttcc gccacggcct cca                                    23

<210> SEQ ID NO 17
<211> LENGTH: 22
<212> TYPE: DNA
<213> ORGANISM: Artificial Sequence
<220> FEATURE:
<223> OTHER INFORMATION: Hes3 forward primer

<400> SEQUENCE: 17
aggtctcttc tggagagaca ct                                     22

<210> SEQ ID NO 18
<211> LENGTH: 20
<212> TYPE: DNA
<213> ORGANISM: Artificial Sequence
<220> FEATURE:
<223> OTHER INFORMATION: Hes3 reverse primer

<400> SEQUENCE: 18
cgctgtccgt ggtgctgcct                                        20

<210> SEQ ID NO 19
<211> LENGTH: 20
<212> TYPE: DNA
<213> ORGANISM: Artificial Sequence
<220> FEATURE:
<223> OTHER INFORMATION: Hes5 forward primer

<400> SEQUENCE: 19
cgactgcgga agccggtggt                                        20

<210> SEQ ID NO 20
<211> LENGTH: 21
<212> TYPE: DNA
<213> ORGANISM: Artificial Sequence
<220> FEATURE:
<223> OTHER INFORMATION: Hes5 reverse primer

<400> SEQUENCE: 20
agcagcttca tctgcgtgtc g                                      21

<210> SEQ ID NO 21
<211> LENGTH: 21
<212> TYPE: DNA
<213> ORGANISM: Artificial Sequence
<220> FEATURE:

<223> OTHER INFORMATION: Frz1 forward primer

<400> SEQUENCE: 21
cgggcagcag tacaacggcg a                    21

<210> SEQ ID NO 22
<211> LENGTH: 21
<212> TYPE: DNA
<213> ORGANISM: Artificial Sequence
<220> FEATURE:
<223> OTHER INFORMATION: Frz1 reverse primer

<400> SEQUENCE: 22
gttctggccc acgcacagct c                    21

<210> SEQ ID NO 23
<211> LENGTH: 21
<212> TYPE: DNA
<213> ORGANISM: Artificial Sequence
<220> FEATURE:
<223> OTHER INFORMATION: Frz3 forward primer

<400> SEQUENCE: 23
ggaatatgga cgtgtcacac t                    21

<210> SEQ ID NO 24
<211> LENGTH: 21
<212> TYPE: DNA
<213> ORGANISM: Artificial Sequence
<220> FEATURE:
<223> OTHER INFORMATION: Frz3 reverse primer

<400> SEQUENCE: 24
gcgagcaaat gacagttctt c                    21

<210> SEQ ID NO 25
<211> LENGTH: 21
<212> TYPE: DNA
<213> ORGANISM: Artificial Sequence
<220> FEATURE:
<223> OTHER INFORMATION: Frz4 forward primer

<400> SEQUENCE: 25
tgagactagt ggatgccgat g                    21

<210> SEQ ID NO 26
<211> LENGTH: 22
<212> TYPE: DNA
<213> ORGANISM: Artificial Sequence
<220> FEATURE:
<223> OTHER INFORMATION: Frz4 reverse primer

<400> SEQUENCE: 26
ccctcttctc tctctttacc tt                   22

<210> SEQ ID NO 27
<211> LENGTH: 20
<212> TYPE: DNA
<213> ORGANISM: Artificial Sequence
<220> FEATURE:
<223> OTHER INFORMATION: Frz5 forward primer

<400> SEQUENCE: 27
ccaggaaatc acggtgccca                      20

```
<210> SEQ ID NO 28
<211> LENGTH: 20
<212> TYPE: DNA
<213> ORGANISM: Artificial Sequence
<220> FEATURE:
<223> OTHER INFORMATION: Frz5 reverse primer

<400> SEQUENCE: 28
cggtcgcagc tcatgcgctc                                                20

<210> SEQ ID NO 29
<211> LENGTH: 20
<212> TYPE: DNA
<213> ORGANISM: Artificial Sequence
<220> FEATURE:
<223> OTHER INFORMATION: Frz7 forward primer

<400> SEQUENCE: 29
acacgaacca agaggacgcg                                                20

<210> SEQ ID NO 30
<211> LENGTH: 20
<212> TYPE: DNA
<213> ORGANISM: Artificial Sequence
<220> FEATURE:
<223> OTHER INFORMATION: Frz7 reverse primer

<400> SEQUENCE: 30
gagccgtcgg acgtgttctg                                                20

<210> SEQ ID NO 31
<211> LENGTH: 21
<212> TYPE: DNA
<213> ORGANISM: Artificial Sequence
<220> FEATURE:
<223> OTHER INFORMATION: Wnt1 forward primer

<400> SEQUENCE: 31
gagtgcaaat gccacgggat g                                              21

<210> SEQ ID NO 32
<211> LENGTH: 20
<212> TYPE: DNA
<213> ORGANISM: Artificial Sequence
<220> FEATURE:
<223> OTHER INFORMATION: Wnt1 reverse primer

<400> SEQUENCE: 32
agctgacgtg gcagcaccag                                                20

<210> SEQ ID NO 33
<211> LENGTH: 20
<212> TYPE: DNA
<213> ORGANISM: Artificial Sequence
<220> FEATURE:
<223> OTHER INFORMATION: Wnt10 forward primer

<400> SEQUENCE: 33
ccgctgacgg ccaacaccgt                                                20

<210> SEQ ID NO 34
<211> LENGTH: 21
<212> TYPE: DNA
<213> ORGANISM: Artificial Sequence
<220> FEATURE:
<223> OTHER INFORMATION: Wnt10 reverse primer
```

<400> SEQUENCE: 34
atcccgagag aacttctctc c                                              21

<210> SEQ ID NO 35
<211> LENGTH: 20
<212> TYPE: DNA
<213> ORGANISM: Artificial Sequence
<220> FEATURE:
<223> OTHER INFORMATION: Wnt11 forward primer

<400> SEQUENCE: 35
ctgatgcgtc tacacaacag                                                20

<210> SEQ ID NO 36
<211> LENGTH: 21
<212> TYPE: DNA
<213> ORGANISM: Artificial Sequence
<220> FEATURE:
<223> OTHER INFORMATION: Wnt11 reverse primer

<400> SEQUENCE: 36
gcagaagtca ggggagctct g                                              21

<210> SEQ ID NO 37
<211> LENGTH: 20
<212> TYPE: DNA
<213> ORGANISM: Artificial Sequence
<220> FEATURE:
<223> OTHER INFORMATION: Gli1 forward primer

<400> SEQUENCE: 37
agggcagctc aaggctcagc                                                20

<210> SEQ ID NO 38
<211> LENGTH: 21
<212> TYPE: DNA
<213> ORGANISM: Artificial Sequence
<220> FEATURE:
<223> OTHER INFORMATION: Gli1 reverse primer

<400> SEQUENCE: 38
tcatctagga tagccacaaa g                                              21

<210> SEQ ID NO 39
<211> LENGTH: 21
<212> TYPE: DNA
<213> ORGANISM: Artificial Sequence
<220> FEATURE:
<223> OTHER INFORMATION: Gli2 forward primer

<400> SEQUENCE: 39
cagcagaggc tgtgcccaag g                                              21

<210> SEQ ID NO 40
<211> LENGTH: 20
<212> TYPE: DNA
<213> ORGANISM: Artificial Sequence
<220> FEATURE:
<223> OTHER INFORMATION: Gli2 reverse primer

<400> SEQUENCE: 40
gcgtgaggaa ttctgggaga                                                20

<210> SEQ ID NO 41
<211> LENGTH: 21

```
<212> TYPE: DNA
<213> ORGANISM: Artificial Sequence
<220> FEATURE:
<223> OTHER INFORMATION: Gli3 forward primer

<400> SEQUENCE: 41
gtgggcttca gtcagcaaga c                                              21

<210> SEQ ID NO 42
<211> LENGTH: 21
<212> TYPE: DNA
<213> ORGANISM: Artificial Sequence
<220> FEATURE:
<223> OTHER INFORMATION: Gli3 reverse primer

<400> SEQUENCE: 42
ctgcaaggaa cttgctttct t                                              21

<210> SEQ ID NO 43
<211> LENGTH: 20
<212> TYPE: DNA
<213> ORGANISM: Artificial Sequence
<220> FEATURE:
<223> OTHER INFORMATION: Patch forward primer

<400> SEQUENCE: 43
tctgctgggt gtactgatgc                                                20

<210> SEQ ID NO 44
<211> LENGTH: 20
<212> TYPE: DNA
<213> ORGANISM: Artificial Sequence
<220> FEATURE:
<223> OTHER INFORMATION: Patch reverse primer

<400> SEQUENCE: 44
agagtccagg tggggctgtt                                                20

<210> SEQ ID NO 45
<211> LENGTH: 21
<212> TYPE: DNA
<213> ORGANISM: Artificial Sequence
<220> FEATURE:
<223> OTHER INFORMATION: Smo forward primer

<400> SEQUENCE: 45
cctcctggtg gagaagatca a                                              21

<210> SEQ ID NO 46
<211> LENGTH: 20
<212> TYPE: DNA
<213> ORGANISM: Artificial Sequence
<220> FEATURE:
<223> OTHER INFORMATION: Smo reverse primer

<400> SEQUENCE: 46
ctggggagat ctctgcctca                                                20

<210> SEQ ID NO 47
<211> LENGTH: 21
<212> TYPE: DNA
<213> ORGANISM: Artificial Sequence
<220> FEATURE:
<223> OTHER INFORMATION: Shh forward primer

<400> SEQUENCE: 47
```
gccatcattc agaggagtct c                                              21

<210> SEQ ID NO 48
<211> LENGTH: 20
<212> TYPE: DNA
<213> ORGANISM: Artificial Sequence
<220> FEATURE:
<223> OTHER INFORMATION: Shh reverse primer

<400> SEQUENCE: 48
cacgaagagc aggtgcgcgg                                                20

<210> SEQ ID NO 49
<211> LENGTH: 21
<212> TYPE: DNA
<213> ORGANISM: Artificial Sequence
<220> FEATURE:
<223> OTHER INFORMATION: Hiwi forward primer

<400> SEQUENCE: 49
catcaatgaa gggatgaccc g                                              21

<210> SEQ ID NO 50
<211> LENGTH: 21
<212> TYPE: DNA
<213> ORGANISM: Artificial Sequence
<220> FEATURE:
<223> OTHER INFORMATION: Hiwi reverse primer

<400> SEQUENCE: 50
tctcactgcc tggctcacga t                                              21

<210> SEQ ID NO 51
<211> LENGTH: 21
<212> TYPE: DNA
<213> ORGANISM: Artificial Sequence
<220> FEATURE:
<223> OTHER INFORMATION: Nucstem forward primer

<400> SEQUENCE: 51
ttccatggga cttacaagga g                                              21

<210> SEQ ID NO 52
<211> LENGTH: 21
<212> TYPE: DNA
<213> ORGANISM: Artificial Sequence
<220> FEATURE:
<223> OTHER INFORMATION: Nucstem reverse primer

<400> SEQUENCE: 52
aggcacctgt ccactcagac c                                              21

<210> SEQ ID NO 53
<211> LENGTH: 20
<212> TYPE: DNA
<213> ORGANISM: Artificial Sequence
<220> FEATURE:
<223> OTHER INFORMATION: Bmi1 forward primer

<400> SEQUENCE: 53
atgcatcgaa caaccagaat                                                20

<210> SEQ ID NO 54
<211> LENGTH: 18
<212> TYPE: DNA
<213> ORGANISM: Artificial Sequence

```
<220> FEATURE:
<223> OTHER INFORMATION: Bmi1 reverse primer

<400> SEQUENCE: 54
tcactttcca gctctcca                                                 18

<210> SEQ ID NO 55
<211> LENGTH: 21
<212> TYPE: DNA
<213> ORGANISM: Artificial Sequence
<220> FEATURE:
<223> OTHER INFORMATION: Musashi1 forward primer

<400> SEQUENCE: 55
cctggttaca cctaccagtt c                                             21

<210> SEQ ID NO 56
<211> LENGTH: 22
<212> TYPE: DNA
<213> ORGANISM: Artificial Sequence
<220> FEATURE:
<223> OTHER INFORMATION: Musashi1 reverse primer

<400> SEQUENCE: 56
tcagtggtac ccattggtga ag                                            22

<210> SEQ ID NO 57
<211> LENGTH: 23
<212> TYPE: DNA
<213> ORGANISM: Artificial Sequence
<220> FEATURE:
<223> OTHER INFORMATION: Oct4 forward primer

<400> SEQUENCE: 57
ctgctgaagc agaagaggat cac                                           23

<210> SEQ ID NO 58
<211> LENGTH: 24
<212> TYPE: DNA
<213> ORGANISM: Artificial Sequence
<220> FEATURE:
<223> OTHER INFORMATION: Oct4 reverse primer

<400> SEQUENCE: 58
cttctggcgc cggttacaga acca                                          24

<210> SEQ ID NO 59
<211> LENGTH: 24
<212> TYPE: DNA
<213> ORGANISM: Artificial Sequence
<220> FEATURE:
<223> OTHER INFORMATION: Prominin1 forward primer

<400> SEQUENCE: 59
aggctacttt gaacattatc tgca                                          24

<210> SEQ ID NO 60
<211> LENGTH: 21
<212> TYPE: DNA
<213> ORGANISM: Artificial Sequence
<220> FEATURE:
<223> OTHER INFORMATION: Prominin1 reverse primer

<400> SEQUENCE: 60
ggcttgtcat aacaggattg t                                             21
```

<210> SEQ ID NO 61
<211> LENGTH: 21
<212> TYPE: DNA
<213> ORGANISM: Artificial Sequence
<220> FEATURE:
<223> OTHER INFORMATION: Integrin alpha-6 forward primer

<400> SEQUENCE: 61
gagttcagtt tcgaaaccaa g                                              21

<210> SEQ ID NO 62
<211> LENGTH: 21
<212> TYPE: DNA
<213> ORGANISM: Artificial Sequence
<220> FEATURE:
<223> OTHER INFORMATION: Integrin alpha-6 reverse primer

<400> SEQUENCE: 62
gccattctgg ttggcaacac a                                              21

<210> SEQ ID NO 63
<211> LENGTH: 20
<212> TYPE: DNA
<213> ORGANISM: Artificial Sequence
<220> FEATURE:
<223> OTHER INFORMATION: ER-alpha forward primer

<400> SEQUENCE: 63
gctgccaacc tttggccaag                                                20

<210> SEQ ID NO 64
<211> LENGTH: 21
<212> TYPE: DNA
<213> ORGANISM: Artificial Sequence
<220> FEATURE:
<223> OTHER INFORMATION: ER-alpha reverse primer

<400> SEQUENCE: 64
ccttctcttc cagagacttc a                                              21

<210> SEQ ID NO 65
<211> LENGTH: 21
<212> TYPE: DNA
<213> ORGANISM: Artificial Sequence
<220> FEATURE:
<223> OTHER INFORMATION: ER-beta forward primer

<400> SEQUENCE: 65
aagagggatg ctcacttctg c                                              21

<210> SEQ ID NO 66
<211> LENGTH: 20
<212> TYPE: DNA
<213> ORGANISM: Artificial Sequence
<220> FEATURE:
<223> OTHER INFORMATION: ER-beta reverse primer

<400> SEQUENCE: 66
ccctcatccc tgtccagaac                                                20

<210> SEQ ID NO 67
<211> LENGTH: 20
<212> TYPE: DNA
<213> ORGANISM: Artificial Sequence
<220> FEATURE:
<223> OTHER INFORMATION: Mucin1 (EMA) forward primer -continued

<400> SEQUENCE: 67
gtaccatcaa tgtccacgac                                              20

<210> SEQ ID NO 68
<211> LENGTH: 20
<212> TYPE: DNA
<213> ORGANISM: Artificial Sequence
<220> FEATURE:
<223> OTHER INFORMATION: Mucin1 (EMA) reverse primer

<400> SEQUENCE: 68
ctacgatcgg tactgctagg                                              20

<210> SEQ ID NO 69
<211> LENGTH: 20
<212> TYPE: DNA
<213> ORGANISM: Artificial Sequence
<220> FEATURE:
<223> OTHER INFORMATION: CK14 forward primer

<400> SEQUENCE: 69
gtgaccatgc agaacctcaa                                              20

<210> SEQ ID NO 70
<211> LENGTH: 21
<212> TYPE: DNA
<213> ORGANISM: Artificial Sequence
<220> FEATURE:
<223> OTHER INFORMATION: CK14 reverse primer

<400> SEQUENCE: 70
tgctgagctg ggactgcagc t                                            21

<210> SEQ ID NO 71
<211> LENGTH: 22
<212> TYPE: DNA
<213> ORGANISM: Artificial Sequence
<220> FEATURE:
<223> OTHER INFORMATION: CK18 forward primer

<400> SEQUENCE: 71
aaggtcattg atgacaccaa ta                                           22

<210> SEQ ID NO 72
<211> LENGTH: 20
<212> TYPE: DNA
<213> ORGANISM: Artificial Sequence
<220> FEATURE:
<223> OTHER INFORMATION: CK18 reverse primer

<400> SEQUENCE: 72
ggatggtttg catggagttg                                              20

<210> SEQ ID NO 73
<211> LENGTH: 20
<212> TYPE: DNA
<213> ORGANISM: Artificial Sequence
<220> FEATURE:
<223> OTHER INFORMATION: CK19 forward primer

<400> SEQUENCE: 73
gacaagattc ttggtgccac                                              20

<210> SEQ ID NO 74

```
<211> LENGTH: 20
<212> TYPE: DNA
<213> ORGANISM: Artificial Sequence
<220> FEATURE:
<223> OTHER INFORMATION: CK19 reverse primer

<400> SEQUENCE: 74
gactgcagct caatctcaag                                          20
```